United States Patent
Cantor

(10) Patent No.: US 8,852,864 B2
(45) Date of Patent: Oct. 7, 2014

(54) METHODS AND COMPOSITIONS FOR THE ANALYSIS OF NUCLEIC ACIDS

(75) Inventor: Charles R. Cantor, Del Mar, CA (US)

(73) Assignee: Sequenom Inc., San Deigo, CA (US)

( * ) Notice: Subject to any disclaimer, the term of this patent is extended or adjusted under 35 U.S.C. 154(b) by 924 days.

(21) Appl. No.: 12/863,169

(22) PCT Filed: Jan. 16, 2009

(86) PCT No.: PCT/US2009/031325
§ 371 (c)(1),
(2), (4) Date: Jan. 27, 2011

(87) PCT Pub. No.: WO2009/092035
PCT Pub. Date: Jul. 23, 2009

(65) Prior Publication Data
US 2011/0124518 A1    May 26, 2011

Related U.S. Application Data

(60) Provisional application No. 61/021,872, filed on Jan. 17, 2008.

(51) Int. Cl.
*C12Q 1/68* (2006.01)
(52) U.S. Cl.
CPC ............ *C12Q 1/6816* (2013.01); *C12Q 1/6869* (2013.01)
USPC ........................................................ 435/6.11
(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,962,037 A | 10/1990 | Jett et al. | |
| 5,750,341 A | 5/1998 | Macevicz et al. | |
| 5,759,773 A | 6/1998 | Tyagi et al. | |
| 5,786,146 A | 7/1998 | Herman et al. | |
| 5,795,782 A | 8/1998 | Church et al. | |
| 5,925,517 A | 7/1999 | Tyagi et al. | |
| 5,998,175 A * | 12/1999 | Akhavan-Tafti | 435/91.5 |
| 6,013,456 A | 1/2000 | Akahavan-Tafti | |
| 6,015,714 A | 1/2000 | Baldarelli et al. | |
| 6,150,097 A | 11/2000 | Tyagi et al. | |
| 6,210,896 B1 | 4/2001 | Chan | |
| 6,214,560 B1 | 4/2001 | Yguerabide et al. | |
| 6,263,286 B1 | 7/2001 | Gilmanshin et al. | |
| 6,267,872 B1 | 7/2001 | Akeson et al. | |
| 6,297,006 B1 | 10/2001 | Drmanac et al. | |
| 6,355,420 B1 | 3/2002 | Chan | |
| 6,362,002 B1 | 3/2002 | Denison et al. | |
| 6,403,311 B1 | 6/2002 | Chan | |
| 6,464,842 B1 | 10/2002 | Golovchenko et al. | |
| 6,506,594 B1 | 1/2003 | Barany et al. | |
| 6,528,258 B1 | 3/2003 | Russell | |
| 6,537,755 B1 | 3/2003 | Drmanac et al. | |
| 6,627,067 B1 | 9/2003 | Branton et al. | |
| 6,673,615 B2 | 1/2004 | Denison et al. | |
| 6,706,204 B2 | 3/2004 | Roitman et al. | |
| 6,723,513 B2 | 4/2004 | Lexow | |
| 6,730,531 B2 | 5/2004 | Park | |
| 6,746,594 B2 | 6/2004 | Akeson et al. | |
| 6,772,070 B2 | 8/2004 | Gilmanshin et al. | |
| 6,864,052 B1 | 3/2005 | Drmanac et al. | |
| 6,927,065 B2 | 8/2005 | Chan et al. | |
| 6,952,651 B2 | 10/2005 | Su | |
| 6,955,901 B2 * | 10/2005 | Schouten | 435/91.1 |
| 7,005,264 B2 | 2/2006 | Su et al. | |
| 7,030,167 B2 | 4/2006 | Gunther | |
| 7,075,161 B2 | 7/2006 | Barth | |
| 7,189,503 B2 | 3/2007 | Akeson et al. | |
| 7,279,337 B2 | 10/2007 | Zhu | |
| 2003/0082600 A1 | 5/2003 | Olek et al. | |
| 2003/0119004 A1* | 6/2003 | Wenz et al. | 435/6 |
| 2003/0180779 A1 | 9/2003 | Lofton-Day et al. | |
| 2005/0019784 A1 | 1/2005 | Su et al. | |
| 2005/0112590 A1 | 5/2005 | Boom et al. | |
| 2005/0130213 A1 | 6/2005 | Morrison | |
| 2006/0019247 A1 | 1/2006 | Su et al. | |
| 2006/0063171 A1 | 3/2006 | Akeson et al. | |
| 2007/0202525 A1 | 8/2007 | Quake et al. | |
| 2009/0202984 A1 | 8/2009 | Cantor | |

FOREIGN PATENT DOCUMENTS

| | | |
|---|---|---|
| WO | WO 2004/078640 | 9/2004 |
| WO | WO 2005/045392 | 5/2005 |
| WO | WO 2006/020775 | 2/2006 |
| WO | WO 2006/092588 | 9/2006 |

OTHER PUBLICATIONS

Anantha, et al., Biochemistry (1998) 37:2709-2714.
Current Protocols in Molecular Biology, John Wiley & Sons, N.Y., 6.3.1-6.3.6 (1989).
Dear Brief Funct Genomic Proteomic 2003; 1: 397-416.
Harris et al. 2008 Science, 320, 106-109.
Innis et al., "PCR Protocols: A Guide to Methods and Applications," (1990).
International Preliminary Report on Patentability mailed on: Jun. 29, 2010 in International Application No. PCT/US2009/031325 filed on Jan. 16, 2009 and published as WO2009/092035 on Jul. 23, 2009.
International Search Report and Written Opinion mailed on: Aug. 28, 2009 in International Application No. PCT/US2009/031325 filed on Jan. 16, 2009 and published as WO2009/092035 on Jul. 23, 2009.
Margulies, M. et al. 2005 Nature 437, 376-380.
Qu & Chaires, Methods Enzymol. (2000) 321:353-369.
Soni and Meller, Progress toward Ultrafast DNA sequencing using Solid-State Nanopores, Clinical Chemistry 53(11):1996-2001 2007.

\* cited by examiner

*Primary Examiner* — Angela M Bertagna
(74) *Attorney, Agent, or Firm* — Grant IP, Inc.

(57) ABSTRACT

Provided herein are compositions and methods for analysis of nucleic acids, including, methods and compositions for genotyping, haplotyping, sequencing and performing other genetic and epigenetic analysis on nucleic acids, for example. In some embodiments, methods and compositions suitable for whole-genome sequencing on single molecules of nucleic acid are provided. In some embodiments, analysis of single molecules of nucleic acid are performed in conjunction with nanopores and/or nanopore devices.

35 Claims, 5 Drawing Sheets

METHODS AND COMPOSITIONS FOR THE ANALYSIS OF NUCLEIC ACIDS

RELATED APPLICATION

This patent application is a national stage of international patent application number PCT/US2009/031325, filed on Jan. 16, 2009, entitled METHODS AND COMPOSITIONS FOR THE ANALYSIS OF BIOLOGICAL MOLECULES, naming Charles R. Cantor as applicant, which claims the benefit of U.S. Provisional Patent Application No. 61/021,872, filed on Jan. 17, 2008, entitled METHODS AND COMPOSITIONS FOR THE ANALYSIS OF BIOLOGICAL MOLECULES, naming Charles R. Cantor as applicant. The entire content of these applications, including all text, tables and drawings, are incorporated herein by reference in jurisdictions permitting such practice.

FIELD OF THE INVENTION

The present invention relates in part to methods and compositions for the analysis of biological molecules, including the analysis of single nucleic acid molecules.

BACKGROUND

Nucleic acid sequencing methods that involve separation of nucleic acid molecules in a gel, such as gel electrophoresis, have been in use since the late 1970's. A traditional method of determining a sequence of nucleotides (i.e., the order of the A, G, C and T nucleotides in a sample) is performed by preparing a mixture of randomly terminated, differentially labeled nucleic acid fragments by degradation at specific nucleotides, or by dideoxy chain termination of replicating strands, so called Sanger dideoxy sequencing. Resulting nucleic acid fragments in the range of 1 to 500 base pairs (bp) then are separated on a gel to produce a ladder of bands where the adjacent bands differ in length by one nucleotide. Advances in nucleic acid analysis technology have included novel fluorescent and chromogenic (e.g., non-radioactive) labels, non-gel based sequence reading technologies (e.g., mass spectrometry, image based methods using charge couple device (CCD) or video cameras, and luminescent nucleotides) and the use of nanopore technology to determine, for example, the sequence of a nucleic acid.

SUMMARY

Until recently, nucleic acid sequencing was a time consuming process that required expensive equipment and the use of hazardous materials. While the speed with which nucleic acid sequence information is generated is increasing, further increases in the rate of determining the sequence of nucleotides, which comprise nucleic acid sequences, would be advantageous for advancement of molecular biology, medicine, and biotechnology. Thus, a problem associated with nucleic acid sequencing technologies is a lack of high speed sequence analysis and control. Nanopore technologies allow for high density sequencing arrays, but certain problems exist, such as detection methods and controlling the speed with which a nucleic acid translocates through a pore, that prevent nanopore technology from achieving resolution and control necessary for broad acceptance. The invention herein provides solutions to these problems. For example, provided herein are methods and compositions that can be utilized with relatively rapid sequencing platforms (e.g., nanopore technology). Sequencing and analysis methods provided herein allow for increased levels of control, resolution, and informational processing capabilities.

Thus, the present invention in part provides methods and processes useful for nucleic acid sequencing, genotyping, haplotyping, sequence copy number determination, detection of specific sequences, identification of insertions, deletions, or translocations, measurement of phenotypic variation, and the like. The invention also in part provides methods and processes useful for determining the methylation state of nucleic acids, and can be used to determine the influence of methylation on genotypic and phenotypic expression. Also provided herein are compositions suitable for use in the methodologies described, which include probes and molecular beacons, for example. Also provided are methods for (i) increasing detection resolution by increasing the number of reference points, and/or (ii) decreasing the speed of nucleic acid translocation (i.e., passage through) a nanopore device.

Thus provided herein is a method for analyzing a nucleic acid, which comprises: (a) contacting a target nucleic acid with a plurality of nucleic acid probes under conditions in which probes having a nucleotide sequence substantially complementary to a subsequence of the target nucleic acid can hybridize to the target nucleic acid ("complementary nucleotide sequence"), where: (i) the complementary nucleotide sequence is located at the 5' or 3' end of each probe; (ii) the ends of each complementary nucleotide sequence of each probe in probe pairs are (1) adjacent to one another when hybridized to the target nucleic acid, (2) are adjacent to an intervening linker probe, (3) do not abut one another and intervening nucleotides are added by an enzyme capable polymerizing nucleotides complementary to the target nucleic acid sequence; (iii) each probe comprises a detector region having a polynucleotide sequence not substantially complementary to a subsequence of the target nucleic acid; (iv) each detector region is located at the 5' or 3' end of each probe and on the end of the probe opposite the complementary nucleotide sequence; (v) the end of a detector region of a first probe of a probe pair is in proximity to the end of a detector region of a second probe in another probe pair, with the proviso that the end of a detector region of one probe in two probe pairs is not in proximity to the end of the detector region of another probe; and (vi) the first probe flanks the second probe when the first probe and second probe are hybridized to the target nucleic acid; (b) ligating the ends of the complementary nucleotide sequences of probe pairs that are adjacent to one another when hybridized to the target nucleic acid; (c) joining the ends of detector regions in proximity to one another, thereby forming a linked probe molecule; (d) passing the linked probe molecule through the pore of a nanopore device; and (e) determining the base sequence of the linked probe molecule, whereby the target nucleic acid is analyzed.

In some embodiments, methods for analysis include, but are not limited to, nucleic acid sequencing, copy number determination, methylation analysis, genotyping, haplotyping, detection of specific sequences, identification of insertions, deletions, or translocations, identification of single nucleotide polymorphisms and sequence variations, detection of allelic variance, measurement of phenotypic variance, or combinations thereof. In certain embodiments, there may be a probe at each end of a linked probe molecule that has a detector region not in proximity to a detector region of another probe. That is, at the end of each linked probe chain (the 5' and 3' ends of the linked probe molecule), the detector portions of the first and last probe in the chain often are not in proximity to the detector region of another probe, and therefore those detector portions often remain unlinked.

In some embodiments a target nucleic acid comprises DNA, and sometimes a target nucleic acid consists of DNA. In certain embodiments a target nucleic acid may comprise RNA, and sometimes, a target nucleic acid consists of RNA. In some embodiments a target nucleic acid may be from a single sample. A target nucleic acid may comprise pooled DNA, in certain embodiments. In some embodiments a target nucleic acid may consist of pooled DNA. In certain embodiments a target nucleic acid comprises pooled RNA, and in certain embodiments a target nucleic acid consists of pooled RNA. That is, RNA or DNA from different samples, organisms, environments, and the like may be combined (i.e., "pooled") prior to subjecting the nucleic acids to methods described herein. In certain embodiments a target nucleic acid may be fragmented DNA. In some embodiments a target nucleic acid may be methylated DNA. In embodiments where the target nucleic acid is methylated, the target nucleic acid may be treated with an agent that converts a non-methylated nucleotide or methylated nucleotide in the target nucleic acid to a detectable entity. Non-methylated cytosine nucleotides may be converted to uracil nucleotides by treatment of the target nucleic acid with the appropriate agent, in some embodiments.

In certain embodiments a probe comprises DNA, and sometimes a probe consists of DNA. In certain embodiments a probe comprises RNA, and sometimes a probe consists of RNA. In certain embodiments a probe comprises polyamine nucleic acids (PNA), and in some embodiments, a probe consists of PNA. In certain embodiments a probe may comprise a detector region, where the detector region generally comprises a detectable moiety. In embodiments where the probe detector region comprises a detectable moiety, the moiety may be selected from the group consisting of: a radioactive agent, a fluorescent agent, a light scattering agent, a molecular beacon, an affinity capture agent, a chemiluminescent agent, a protein agent, a peptide agent, a chromogenic agent, a biomolecule, and a combination thereof.

In some embodiments detector portions of probes in proximity to one another may be joined by chemical ligation. In certain embodiments detector portions of probes in proximity to one another may be joined by cross-linking. In some embodiments the cross-linking may be effected by UV light, a non-specific cross-linking agent, a sequence specific cross-linking agent, or a combination thereof. Joining (e.g., ligation, chemical ligation or cross-linking) of probes with other probes, nucleotides or linker primers often forms a linked probe molecule.

In certain embodiments a linked probe molecule may be passed through a nanopore device by a gradient. In some embodiments the gradient is an electrical gradient, chemical gradient, magnetic gradient, or a combination thereof. The base sequence of linked probes is determined by a nucleotide sequencing method in certain embodiments. In some embodiments the nucleotide sequencing method is pyrosequencing or sequencing by synthesis.

Certain embodiments and features of the invention are described in greater detail in the following description, claims and drawings.

BRIEF DESCRIPTION OF THE DRAWINGS

The drawings illustrate embodiments of the invention and are not limiting. It should be noted that for clarity and ease of illustration, these drawings are not made to scale and that in some instances various embodiments of the invention may be shown exaggerated or enlarged to facilitate an understanding of particular embodiments.

FIG. 1A illustrates an embodiment in which a nucleic acid is designed as an allele specific probe. FIG. 1B illustrates an embodiment in which two probes, with adjacent regions of interest, are used to identify a specific allele and may also be used to identify nucleotides immediately adjacent to a single nucleotide polymorphism. FIG. 1C illustrates an embodiment in which probes bind adjacent to a region of sequence variation.

FIG. 4A is a line diagram of certain aspects of a nanopore device associated with detecting changes in electrical voltage or ion flow at or around the opening of a nanopore. FIG. 4B illustrates how a nanopore device can be used to detect signal generating moiety patterns of double stranded nucleic acid signal-generating complexes. FIG. 4C illustrates an indirect method of sequence determination by moiety detection where molecular beacons or other detectable moieties are unzipped or removed from a double stranded target sequence by a protein nanopore, and the act of unzipping controls the rate of nucleic acid translocation through the nanopore.

DETAILED DESCRIPTION

Figure 1:
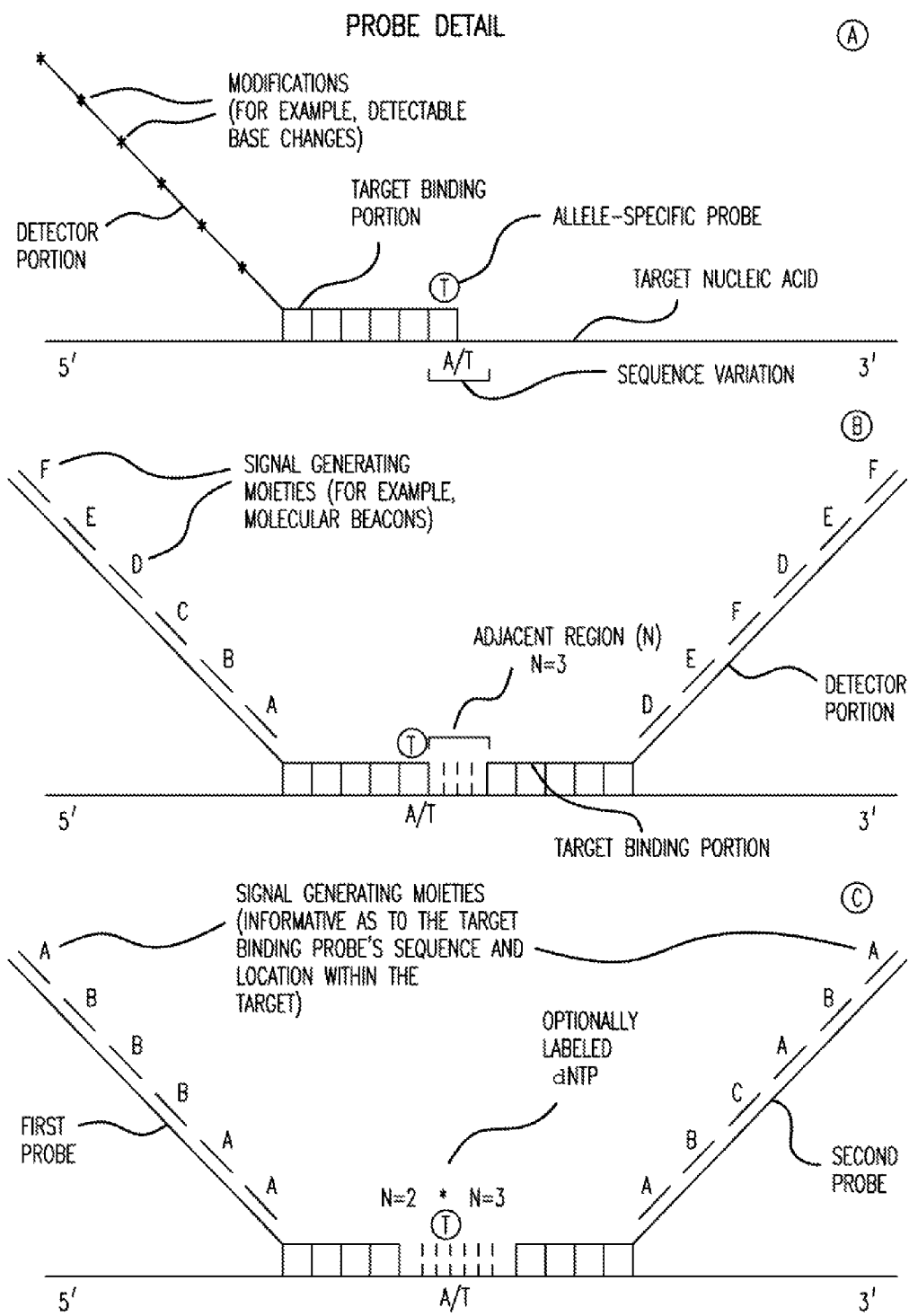
FIG. 1 depicts an example of a probe.

Recently discovered methodologies allow the use of nanopore devices for nucleic acid analysis. Nanopore-based nucleic acid analysis methods have been developed that allow single molecule sequencing, but some difficulties exist with the technology. Examples of the difficulties associated with using nanopore devices are speed of translocation and detection resolution. Nucleic acids travel through a nanopore at a very high rate, making accurate and reproducible sequence reading a challenge. Products and processes described herein can provide solutions to challenges associated with the use of nanopore-based nucleic acid analysis methods (e.g., speed and resolution) and other sequence elucidation methods. Thus, provided herein are products and processes useful for various types of nucleic acid and genomic analysis, including, but not limited to, genotyping, haplotyping, nucleic acid sequence variation analysis, nucleic acid sequencing (short range and long range), methylation status determination, methylation based sequence variation analysis, and the like.

Samples and Target Nucleic Acids

The term "sample" as used herein is meant to include both biological and environmental samples that include nucleic acids. A sample may be collected from an organism, mineral or geological site (e.g., soil, rock, mineral deposit, combat theater, industrial sample), forensic site (e.g., crime scene, contraband or suspected contraband), or a paleontological or archeological site (e.g., fossil, or bone) for example. A sample may be a "biological sample," which refers to any material obtained from a living source or formerly-living source, for example, an animal such as a human or other mammal, a plant, a bacterium, a fungus, a protist or a virus. A sample may include a specimen of synthetic origin. Biological samples may include umbilical cord blood, chorionic villi, amniotic fluid, cerbrospinal fluid, spinal fluid, lavage fluid (e.g., bronchoalveolar, gastric, peritoneal, ductal, ear, athroscopic), biopsy sample, urine, feces, sputum, saliva, nasal mucous, prostate fluid, semen, lymphatic fluid, bile, tears, sweat, breast milk, breast fluid, embryonic cells and fetal cells. In some embodiments, a biological sample may be blood, and sometimes plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

Samples may contain one or more than one source of target nucleic acid. The presence or absence of a target can be measured quantitatively or qualitatively. Targets can come in a variety of different forms including, for example, simple or complex mixtures, or in substantially purified forms. For example, a target can be part of a sample that contains other components or can be the sole or major component of the sample. Therefore, a target can be a component of a whole cell or tissue, a cell or tissue extract, a fractionated lysate thereof or a substantially purified molecule. Also a target can have a known or unknown sequence or structure.

The terms "target" or "target nucleic acid" as used herein refer to a molecule from a sample that is detected, sequenced or measured or the function, interactions or properties of the molecule is studied. A target sometimes is a protein, peptide or nucleic acid. Target nucleic acids may contain one or more regions of interest. As used herein, the terms "region(s) of interest" and "sequence of interest" refers to nucleic acid subsequence or species for which the processes described herein are being used, to facilitate further identification, quantification or analysis. Examples of regions of interest include, without limitation, mutations, single nucleotide polymorphisms, substitution of one or more contiguous nucleotides, deletions of one or more nucleotides, insertions of one of more nucleotides, microsatellites, repeat nucleotide regions, heterozygous alleles, homozygous alleles, modified nucleotides (methylated, for example) and the like. Therefore, a target includes essentially any nucleic acid molecule for which a probe or assay exists, or can be produced by one skilled in the art, including indirect assays that use other biomolecules as a means of obtaining results. The terms "biomolecule" or "biomolecules" as used herein refers to material from a biological sample, or reactive with a biological sample, and may be from the same or a different source as the target of interest. In some embodiments a biomolecule may be a member of a binding pair (e.g. biotin/streptavidin, other binding pairs are described below). A target can be a macromolecule such as a nucleic acid, for example.

The terms "nucleic acid" and "nucleic acid molecule" may be used interchangeably throughout the disclosure. The terms refer to nucleic acids from any source or composition, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A target nucleic acid in some embodiments can be from a single chromosome (e.g., a nucleic acid sample may be from one chromosome of a sample obtained from a diploid organism). The term also may include, as equivalents, derivatives, variants and analogs of RNA or DNA made from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil.

Target (or sample) nucleic acid may be derived from one or more sources (e.g., cells, soil, etc.) by methods known to the person of ordinary skill in the art. Cell lysis procedures and reagents are commonly known in the art and may generally be performed by chemical, physical, or electrolytic lysis methods. For example, chemical methods generally employ lysing agents to disrupt the cells and extract the nucleic acids from the cells, followed by treatment with chaotropic salts. Physical methods such as freeze/thaw followed by grinding, the use of cell presses and the like are also useful. High salt lysis procedures are also commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, solution 1 can contain 15 mM Tris, pH 8.0; 10 mM EDTA and 100 ug/ml Rnase A; solution 2 can contain 0.2N NaOH and 1% SDS; and solution 3 can contain 3M KOAc, pH 5.5. These procedures can be found in Current Protocols in Molecular Biology, John Wiley & Sons, N.Y., 6.3.1-6.3.6 (1989), incorporated herein in its entirety. A source containing target nucleic acid(s) may contain one or a plurality of target nucleic acids. A plurality of target nucleic acids as described herein refers to at least 2 target nucleic acids and includes nucleic acid sequences that may be identical or different. That is, the target nucleic acids may all be representative of the same nucleic acid sequence, or may be representative of two or more different nucleic acid sequences (e.g., from 1, 2, 3, 4, 5, 6, 7, 8, 9, 10, 11, 12, 13, 14, 15, 16, 17, 18, 19, 20, 50, 100, 1000 or more sequences).

Target nucleic acid also may be isolated at a different time point as compared to another target nucleic acid, where each of the samples are from the same or a different source. A target nucleic acid may be from a nucleic acid library, such as a cDNA or RNA library, for example. A target nucleic acid may be a result of nucleic acid purification or isolation and/or amplification of nucleic acid molecules from the sample. Target nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Target nucleic acid may be provided for conducting methods described herein without processing of the sample(s) containing the nucleic acid in certain embodiments. In some embodiments, target nucleic acid is provided for conducting methods described herein after processing of the sample(s) containing the nucleic acid. For example, a target nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated target nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to target nucleic acid provided that contains fewer nucleic acid species than in the sample source from which the target nucleic acid is derived. A composition comprising target nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Target nucleic acid also may be processed by subjecting nucleic acid to a method that generates nucleic acid fragments, in certain embodiments, before providing target nucleic acid for a process described herein. In some embodiments, target nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure by the person of ordinary skill. In certain embodiments, target nucleic acid of a relatively shorter length can be utilized to analyze sequences that contain little sequence variation and/or contain relatively large amounts of known nucleotide sequence information. In some embodiments, target nucleic acid of a relatively longer length can be utilized to analyze sequences that contain greater sequence variation and/or contain relatively small amounts of unknown nucleotide sequence information.

Target nucleic acid fragments may contain overlapping nucleotide sequences, and such overlapping sequences can facilitate construction of a nucleotide sequence of the previously non-fragmented target nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Target nucleic acid may be partially fragmented (e.g., from an incomplete or terminated specific cleavage reaction) or fully fragmented in certain embodiments.

Target nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment target nucleic acid include, without limitation, contacting target nucleic acid with apparatus that expose nucleic acid to shearing force (e.g., passing nucleic acid through a syringe needle; use of a French press); exposing target nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Target nucleic acid may be specifically cleaved by contacting the nucleic acid with one or more specific cleavage agents. The term "specific cleavage agent" as used herein refers to an agent, sometimes a chemical or an enzyme, that can cleave a nucleic acid at one or more specific sites. Specific cleavage agents often cleave specifically according to a particular nucleotide sequence at a particular site.

Examples of enzymic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EcIX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I.); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Target nucleic acid may be treated with a chemical agent, and the modified nucleic acid may be cleaved. In non-limiting examples, target nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, "fragmentation" or "cleavage" refers to a procedure or conditions in which a nucleic acid molecule, such as a nucleic acid target gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid target gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid target gene molecule or the portion of an amplified product thereof containing the corresponding nucleotide sequence of a nucleic acid target gene molecule. For example, it is within the scope of the present methods, compounds and compositions, that an amplified product can contain one or more nucleotides more than the amplified nucleotide region of the nucleic acid target gene sequence (e.g., a primer can contain "extra" nucleotides such as a transcriptional initiation sequence, in addition to nucleotides complementary to a nucleic acid target gene molecule, resulting in an amplified product containing "extra" nucleotides or nucleotides not corresponding to the amplified nucleotide region of the nucleic acid target gene molecule). In such an example, the fragments or cleaved products corresponding to the nucleotides not arising from the nucleic acid target gene molecule will typically not provide any information regarding methylation in the nucleic acid target gene molecule. One skilled in the art can therefore understand that the fragments of an amplified product used to provide methylation information in the methods provided herein may be fragments containing one or more nucleotides arising from the nucleic acid target gene molecule, and not fragments containing nucleotides arising solely from a sequence other than that in the nucleic acid target gene molecule. Accordingly, one skilled in the art will understand the fragments arising from methods, compounds and compositions provided herein to include fragments arising from portions of amplified nucleic acid molecules containing, at least in part, nucleotide sequence information from or based on the representative nucleic acid target gene molecule.

As used herein, the term "complementary cleavage reactions" refers to cleavage reactions that are carried out on the same target nucleic acid using different cleavage reagents or by altering the cleavage specificity of the same cleavage reagent such that alternate cleavage patterns of the same target or reference nucleic acid or protein are generated. In certain embodiments, target nucleic acid may be treated with one or more specific cleavage agents (e.g., 1, 2, 3, 4, 5, 6, 7, 8, 9, 10 or more specific cleavage agents) in one or more reaction vessels (e.g., target nucleic acid is treated with each specific cleavage agent in a separate vessel).

Target nucleic acid also may be exposed to a process that modifies certain nucleotides in the nucleic acid before providing target nucleic acid for a method described herein. A process that selectively modifies nucleic acid based upon the methylation state of nucleotides therein can be applied to target nucleic acid. The term "methylation state" as used herein refers to whether a particular nucleotide in a polynucleotide sequence is methylated or not methylated. Methods for modifying a target nucleic acid molecule in a manner that reflects the methylation pattern of the target nucleic acid molecule are known in the art, as exemplified in U.S. Pat. No. 5,786,146 and U.S. patent publications 20030180779 and 20030082600. For example, non-methylated cytosine nucleotides in a nucleic acid can be converted to uracil by bisulfite treatment, which does not modify methylated cytosine. Non-limiting examples of agents that can modify a nucleotide sequence of a nucleic acid include methylmethane sulfonate, ethylmethane sulfonate, diethylsulfate, nitrosoguanidine (N-methyl-N'-nitro-N-nitrosoguanidine), nitrous acid, di-(2-chloroethyl)sulfide, di-(2-chloroethyl)methylamine, 2-aminopurine, t-bromouracil, hydroxylamine, sodium bisulfite, hydrazine, formic acid, sodium nitrite, and 5-methylcytosine DNA glycosylase. In addition, conditions such as high temperature, ultraviolet radiation, x-radiation, can induce changes in the sequence of a nucleic acid molecule. Target nucleic acid may be provided in any form useful for conducting a sequence analysis or manufacture process described herein, such as solid or liquid form, for example. In certain embodiments, target nucleic acid may be provided in a liquid form optionally comprising one or more other components, including without limitation one or more buffers or salts selected by the person of ordinary skill.

Probes

Probes useful for detection, quantification, sequencing and analysis of target nucleic acids are provided in embodiments described herein. In some embodiments, probes are used in sets, where a set contains at least a pair of probes. In some embodiments a set of probes includes a third nucleic acid, used as a linker (i.e., a primer or oligonucleotide) that can reduce non-specific ligation of probes. Such third nucleic acids can reduce non-specific ligation by requiring two successful ligation events to generate a signal generating complex. In some embodiments, probes are not used in sets, for specific applications, such as detection of a specific sequence. A plurality of probe pairs may constitute a probe set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of probe sets, each set comprising a pair of probes and a linker nucleic acid, may be used.

The term "probe", as used herein refers to a nucleic acid that comprises a nucleotide sequence capable of hybridizing or annealing to a target nucleic acid, at or near (i.e., adjacent to) a specific region of interest. Probes can allow for specific determination of a target nucleic acid nucleotide sequence or detection of the target nucleic acid or feature thereof, for example. The term "specific" or "specificity", as used herein, refers to the binding or hybridization of one molecule to another molecule, such as a probe for a target polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules.

Figure 3:
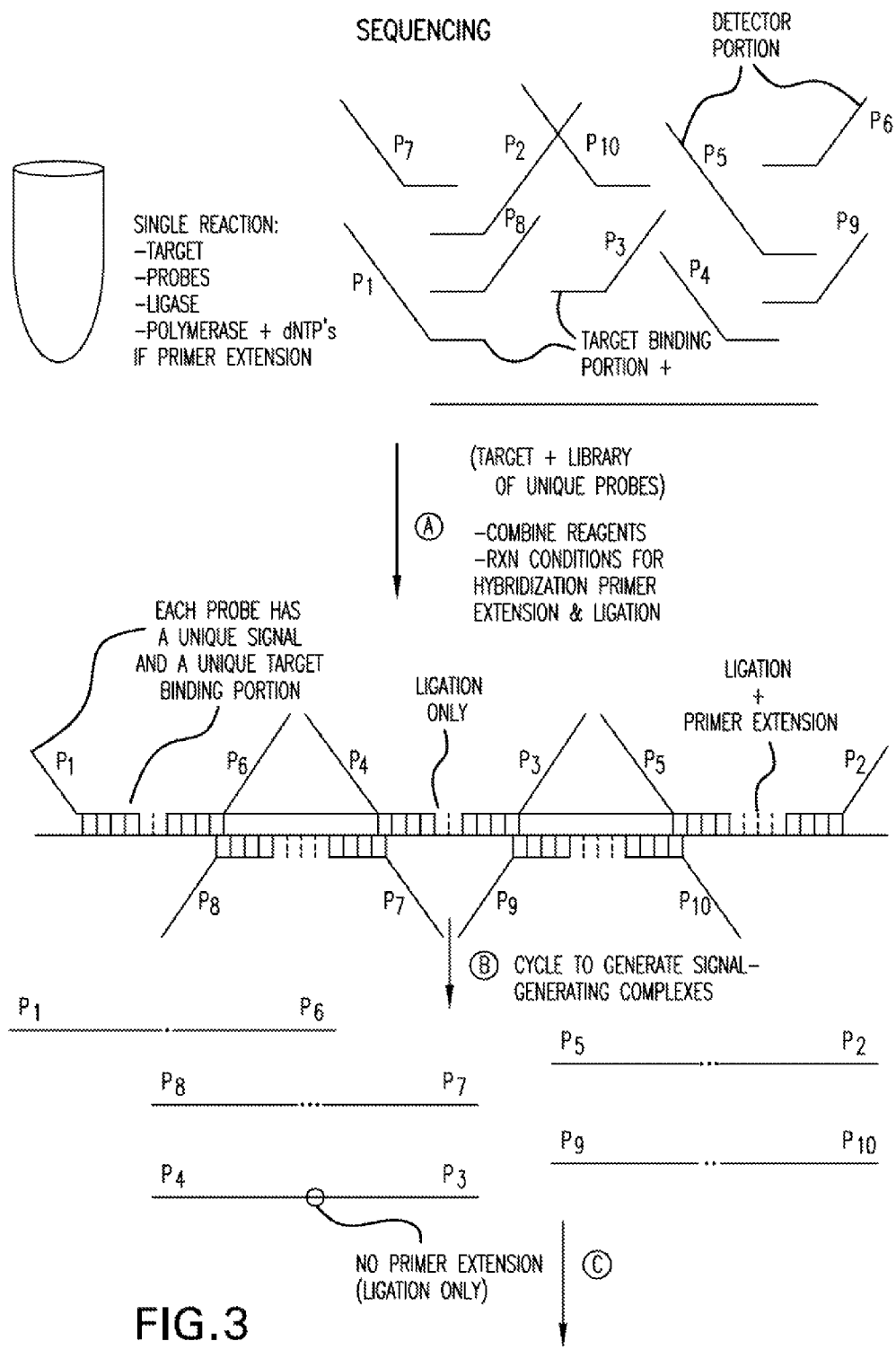
FIGS. 3A-3D depicts a sequencing method.
Figure 3:
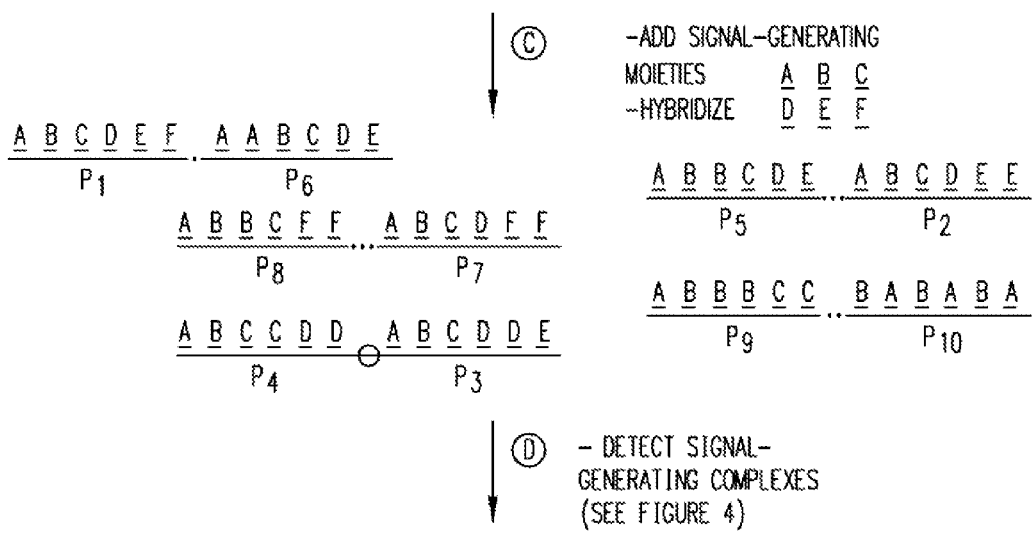

As used herein, the term "adjacent to" refers to a distance or region between the end of a probe and a nucleotide, or the end of a probe and the end of a primer, linker oligonucleotide, or another probe. For example, probes P3 and P4 in FIG. 3 are adjacent to one another when they are hybridized to target nucleic acid. The distance between the ends of adjacent probes, for example, often is measured in terms of the number of nucleotide base spaces between the probe ends. A distance between the end of a probe, and the end of another probe, for example, is sufficiently small such that the likelihood of interaction (direct or indirect) is increased, in certain embodiments. That is, probes are sufficiently close to each other that ligation, polymerization of intervening nucleotides, or joining (e.g., non-DNA ligase mediated ligation or cross-linking) of non-annealed detector portions, may occur with a high rate of success, in some embodiments. The term "a high rate of success" means that the event or reaction proceeds to its desired conclusion (i.e., completion) greater than 70% of the time, greater than 75% of the time, greater than 80% of the time, greater than 85% of the time, greater than 90% of the time, greater than 95% of the time, or greater than 99% of the time. The distance or range between the end of a probe and an adjacent nucleotide, or the end of a primer, linker oligonucleotide, or another probe, may be measured in nucleotides or in nanometers or micrometers (e.g., for non-annealed detector portions), in certain embodiments. For example, the range (in nucleotides) between the ends of adjacent probes hybridized to a target nucleic acid can be 0 nucleotides, 1 nucleotide, 2 nucleotides, 3 nucleotides, 4 nucleotides, 5 nucleotides or more (e.g., up to about 1000 nucleotides) in some embodiments. The range (in physical distance) between the ends of adjacent probes hybridized to a target nucleic acid can be in the range from about 0 nanometers to about 100 nanometers (e.g. about 0, 0.1, 0.2, 0.3, 0.4, 0.5, 0.6, 0.7, 0.8, 0.9, 1.0, 2, 3, 4, 5, 10, 20, 30 nanometers, up to about 100 nanometers), in certain embodiments. Such distances sometimes are mean, average or nominal distances.

The terms "flank" and "flanking" as used herein refer to two probes, where each are not members of the same probe pair, and where the end of the detection region of each probe is capable of being in proximity with the other when the two probes are hybridized to a target nucleic acid. There often is no intervening probe that hybridizes to a target nucleic acid between two flanking probes. For example, in FIG. 3, P4 and P6 flank one another when they are hybridized to target nucleic acid. The term "proximity" as used herein refers to the capability of the ends of detection regions of flanking probes being in substantial contact with one another at certain points in time. In some embodiments, the ends of detection regions of flanking probes are in proximity when they are about 0 nanometers to about 100 nanometers apart from one another (e.g. about 0, 0.1, 0.2, 0.3, 0.4, 0.5, 0.6, 0.7, 0.8, 0.9, 1.0, 2, 3, 4, 5, 10, 20, 30 nanometers, up to about 100 nanometers), in certain embodiments (such distances sometimes are mean, average or nominal distances).

As used herein "substantially complementary" refers to probes or primers that are sufficiently complementary to hybridize with nucleic acid target molecules having a specific sequence under hybridization conditions. Probes and primers often are designed to have sufficient complementarity and hybridize to a subsequence of a target nucleic acid molecule and permit amplification or sequencing of the nucleic acid target gene molecule. For example, a probe or primer used in methods disclosed herein can be 100% complementary with the nucleic acid target gene molecule. Substantially complementary sequences may be 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

The term "joining" or "cross-linking" as used herein refers to a physical linking of two or more nucleic acid molecules, sometimes in a manner not mediated by DNA ligase. Joining or cross-linking may occur through the use of a cross-linking agent or a chemical reaction, sometimes referred to as a "chemical ligation" (e.g. PNA "ligation" at the amine site). Joining also may be accomplished by reacting members of a binding pair (or biomolecules) joined to an end of each of two nucleic acids. In some embodiments, the product of a joining or cross-linking process is a covalent link, or a non-covalent link in certain embodiments. In some embodiments cross-linking may join the non-annealed 3' or 5' detector portions of flanking nucleic acid probes, to form linked probe molecules. Cross-linking may be accomplished in a variety of manners, including formation of hydrogen bonds, ionic and covalent bonds, or van der Wals forces. Non-limiting examples of cross-linking agents or methods that may be used with embodiments described herein are, UV radiation, esterification, hydrolysis, intercalating agents, neoplastic agents, formaldehyde, formalin and 6-bromo-5,5-dimethoxyhexanohydrazide (i.e. preference for C-G cross-links and RNA to complementary DNA).

As used herein, "nucleotide synthesis conditions" in the context of primer hybridization refer to conditions in which a primer anneals to a nucleic acid molecule (e.g., in a filling-in process described above, or extension, linear amplification or exponential amplification process). Exemplary nucleotide synthesis conditions are 10 mM TrisHCl pH 8.3, 1.5 mM MgCl, 50 mM KCl, 62° C. Other exemplary nucleotide synthesis conditions are 16.6 mM ammonium sulfate, 67 mM Tris pH 8.8, 6.7 mM MgCl, 10 mM 2-mercaptoethanol, 60° C. Those of skill in the art are familiar with parameters that affect hybridization; such as temperature, probe or primer length and composition, buffer composition and pH, and salt concentration can readily adjust these parameters to achieve specific hybridization of a nucleic acid to a target sequence.

A probe is "capable of hybridizing" to a nucleic acid sequence if at least one region of the probe shares substantial sequence identity with at least one region of the complement of the nucleic acid sequence. As referred to herein, "substantially identical" with respect to sequences refers to nucleotide sequences sharing a certain amount of sequence identity to each other, target nucleic acids and probes for example. Included are nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. It should be noted that for the purpose of determining sequence identity of a DNA sequence and a RNA sequence, U and T are considered the same nucleotide. For example, a probe comprising the sequence ATCAGC is capable of hybridizing to a target RNA sequence comprising the sequence GCUGAU.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a probe, or primer, to a nucleic acid molecule having a sequence complementary to the probe or primer compared to hybridization to a nucleic acid molecule not having a complementary sequence. For example, specific hybridization includes the hybridization of a probe to a target nucleic acid sequence that is complementary to the probe.

Base modifications also may include moieties that increase the stringency of hybridization or increase the melting temperature of the detector oligonucleotide. The term "stringent hybridization condition" as used herein, refers to hybridization conditions that minimize non-specific or mismatched binding of probe and nucleic acid at non-complementary sequences. Non limiting examples of stringent hybridization conditions include hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids or detector molecules that may be heat labile.

Probes can be of synthetic or natural origin, synthesized oligonucleotides or nucleic acid fragments, respectively, for example. The term "oligonucleotide" as used herein refers to linear oligomers of natural or modified nucleosidic monomers linked by phosphodiester bonds or analogs thereof, and sometimes probes are oligonucleotides. Oligonucleotides can include deoxyribonucleosides, ribonucleosides, anomeric forms thereof, polyamine nucleic acids (PNAs), and the like, and are capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60, or more. Probes (i.e., DNA fragments, synthetic probes (DNA/RNA), primers, oligonucleotide probes, oligonucleotide primers) useful for embodiments described herein may be in the range of about 10 to about 500 nucleotides in length (e.g., about 10, 15, 20, 25, 30, 35, 40, 45, 50, 55, 60, 65, 70, 75, 80, 85, 90, 95, 100, 200, 300, 400, to about 500 nucleotides).

Detection of the target nucleic acid is accomplished through the observation of a detectable label or "signal generating moiety" in some embodiments. The term "signal-generating" as used herein refers to any atom or molecule that can provide a detectable or quantifiable effect, and that can be attached to a nucleic acid. In certain embodiments, the detection moiety may be a moiety characterized by a unique light signal, a fluorescent signal, a luminescent signal, an electrical property, a chemical property, a magnetic property and the like.

Detection moieties include, but are not limited to, nucleotides (labeled or unlabelled), compomers, sugars, peptides, proteins, antibodies, chemical compounds, conducting polymers, binding moieties such as biotin, mass tags, colorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like, some of which are further described below. In some embodiments a probe may contain a signal-generating moiety that hybridizes to a target and alters the passage of the target nucleic acid through a nanopore, as the means of or as an aid to, signal generation (e.g., alters the speed or time through a pore of known size).

In some embodiments probes may include a detectable entity or label (e.g., also referred to as signal generating moiety). The terms "entity" or "label" may be used interchangeably throughout this document. In certain embodiments probes may include more than one detectable label, and in certain embodiments each label may be independently informative. That is, each label may provide information about different aspects of a particular target or region of interest, for example one label may provide sequence information and another methylation status, or location. The label may be incorporated as part of the synthesis of the probe, or added on prior to using the probe (e.g., end-labeling). Non-limiting examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., 125I, 131I, 35S, 31P, 32P, 33P, 14C, 3H, 7Be, 28Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine); quantum dots (e.g., U.S. Pat. Nos. 6,730,531 and 7,465,595); and other cofactors or biomolecules such as digoxigenin, streptavidin, biotin, affinity capture moieties and the like. In some embodiments a nucleotide may be labeled with an affinity capture moiety.

A probe also may refer to a polynucleotide sequence that hybridizes to a subsequence of a target nucleic acid template and facilitates the detection of a detector oligonucleotide, as with molecular beacons, for example. The term "molecular beacon" as used herein refers to detectable molecule, wherein the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments a molecular beacon can be a single-stranded oligonucleotide capable of forming a stem-loop structure, where the loop sequence may be complementary to a target nucleic acid sequence of interest and is flanked by short complementary arms that can form a stem. The oligonucleotide may be labeled at one end with a fluorophore and at the other end with a quencher molecule. In the stem-loop conformation, energy from the excited fluorophore is transferred to the quencher, through long-range dipole-dipole coupling similar to that seen in fluorescence resonance energy transfer, or FRET, and released as heat instead of light. When the loop sequence is hybridized to a specific target sequence, the two ends of the molecule are separated and the energy from the excited fluorophore is emitted as light, generating a detectable signal. Molecular beacons offer the added advantage that removal of excess probe is unnecessary due to the self-quenching nature of the unhybridized probe. In some embodiments molecular beacon probes can be designed to discriminate or tolerate mismatches between the loop and target sequences by modulating the relative strengths of the loop-target hybridization and stem formation. As referred to herein, the term "mismatched nucleotide" or a "mismatch" refers to a nucleotide that is not complementary to the target sequence at that position or positions. A probe may have at least one mismatch, but can also have 2, 3, 4, 5, 6 or 7 or more mismatched nucleotides.

Thus, probes (conventional or molecular beacon type) that potentially discriminate between allelic and phenotypic variants (e.g., nucleotide sequence variations, of any kind, that may or may not change levels of expression or function of protein product, for example) may be designed. In some embodiments various metals may be used as an alternative fluorophore quencher (e.g., gold nanoparticles for example). In some embodiments the length of a molecular beacon probe is in the range of about 10 to about 100 nucleotides in length, and more specifically, between about 15 to 50 nucleotides in length (e.g., about 10, 15, 20, 25, 30, 35, 40, 45, 50, 55, 60, 65, 70, 75, 80, 85, 90, 95, to about 100 nucleotides), with stem sequences (the complementary regions that form the stem structure) that may be in the range of about 3 to about 7 nucleotides in length (e.g., stem sequences about 3, 4, 5, 6, or 7 nucleotides in length).

In FIGS. 1A-1C, a target nucleic acid is shown as the horizontal line, in the conventional 5' to 3' orientation. Vertical lines between the target nucleic acid and the "probe" are representative of conventional Watson-Crick complementary base pairing between nucleotides on the individual nucleic acid molecules. As used herein, "complementary base pairs" or "complementary base pairing" refers to Watson-Crick base pairs (e.g., G to C and A to T in DNA and G to C and A to U in RNA) or the equivalent thereof when non-natural or atypical nucleotides are used. Two nucleic acid strands that are complementary contain complementary base pairing. A probe is not complementary when mismatches such as G-T, G-A, C-T or C-A arise when a probe or primer hybridizes to a nucleic acid target gene molecule.

FIG. 1A illustrates an embodiment in which a nucleic acid is designed as an allele specific probe. Additional probe details are illustrated in FIGS. 1A-1C. Illustrated on the line representing the target nucleic acid is a region of sequence variation (shown as A/T in FIG. 1A). Regions of single nucleotide changes (also referred to as single nucleotide polymorphisms or SNP's) are common in organisms and in certain instances are correlated with predisposition to certain disease conditions (e.g., breast cancer, obesity, and the like). The allele specific probe illustrated in FIG. 1A has a complementary sequence at its 5' end to allow hybridization to alleles containing the nucleotide A at the indicated position (i.e., the probe has the complementary base pairing T), but due to the design of the probe, will not hybridize alleles that have the nucleotide T, at the indicated position. In this specific embodiment, the allele specific recognition sequence is located in the target binding portion of the probe, as illustrated in FIG. 1A. In some embodiments an allele specific recognition sequence may be located adjacent to the target-binding portion of the probe and is sometimes not hybridized by the probe.

Probes useful for the embodiments described herein also comprise a detector portion, as illustrated in FIG. 1A. The detector may be used to provide information regarding the probe, the target or combinations thereof, for example a signal generated by a detector may indicate the presence or absence of a specific allele. In the embodiment illustrated in FIG. 1A, the detector portion of the probe includes modifications (detectable base changes, for example) that allow the probe to be detected. The term "modified" as used herein refers to a probe or target nucleic acid that has been altered to include a detection feature. The term "base modification" as used herein refers to alterations of the detector oligonucleotide at the molecular level (e.g., base moiety, sugar moiety or phosphate backbone). Base modifications include, but are not limited to, the introduction of cleavage blockers or cleavage inducers, the introduction of minor groove binders, isotopic enrichment, isotopic depletion, the introduction of deuterium, and halogen modifications.

In some embodiments an allele specific probe may be hybridized to sample nucleic acid, to detect the presence or absence of a particular allele, for example, as illustrated in FIG. 1. Using stringent hybridization conditions, the probe and target are annealed, the signal-generating moieties separated (i.e., washed) and the results analyzed. Presence of the allele of interest may be indicated by the presence of detectable label after stringent hybridization and washing. Absence of any detectable label may be indicative that the sequence of interest was not present in the sample. Methods used to detect the detector portion of the probe (e.g., probe with detectable label), are dependent on the nature of the label or detector molecule and are readily available to those of skill in the art, particularly when detectable labels are commercially purchased for incorporation into nucleic acid probes. Non-limiting examples of methods of detection include detection of radioactive label, detection of luminescence or fluorescence, identification of specific tags, and the like.

FIG. 1B illustrates an embodiment in which two probes, with adjacent regions of interest, are used to identify a specific allele and may also be used to identify nucleotides immediately adjacent to a single nucleotide polymorphism. The probes illustrated in FIG. 1B have a target binding portion and a detectable portion ("detector") that includes signal generating moieties (segments A-F). In the embodiment illustrated in FIG. 1B (and similarly represented in FIG. 2, middle panel, and FIG. 3, the panel below (A)), the probes are configured such that the detector portion may be 5' or 3' of the target binding portion of the probe. This facilitates ligation of abutting or adjacent hybridized probe pairs, while allowing for joining of non-annealed detector portions. The signal generating moieties may act as detectors (i.e., can be detected, quantified, measured and the like) as previously described, or may act as detectors that provide additional, specific information regarding sequences present in the target nucleic acid as well as the location of the sequences within the target nucleic acid for example, and as such provide additional sequence or structural information by their presence or absence. Additionally, joining adjacent detector regions may also provide an additional level of information regarding nucleotide sequences in or near the target nucleic acid region of interest.

In some embodiments, the signal generating moieties may be molecular beacons that bind to nucleotide sequences in the detector portion of the probe, and are informative as to the target binding probes sequence and location within the target. It will be understood that the additional specific information to which the various signal generating moieties may pertain, include, but are not limited to, chromosomal information (particular chromosome, particular arm of chromosome, particular band in chromosome), specific species of microsatellite, disease marker (as might be associated with an SNP, chromosomal insertion, deletion, or translocation), geographical distribution, ethnic distribution, and the like. Additionally, correlation between particular signal generating moieties, the sequences contained therein and genetic information databases may allow the design of simple probes that provide relatively large amounts of information in a single or few experiments. The method embodiments described herein may also be used to generate sequence information directly (by sequencing, sequencing by synthesis, or nanopore methods) or indirectly (through sequence information associated with signal generating moieties or the manner in which hybridized signal generating moieties alter the passage of a target nucleic acid through a nanopore).

In the embodiment illustrated in FIG. 1B, the two probes bind to target nucleic acid sequences adjacent to each other but not directly abutting one another. That is, there is a region of unbound nucleic acid sequence between the probes. In some embodiments, probes may bind adjacent to a region of sequence variation, as illustrated in FIG. 1C. In the embodiment illustrated in FIG. 1C, the two probes bind to a target nucleic acid sequence, adjacent to each other but not directly abutting one another, and neither probe engages the variant nucleotide. That is, there is a region of unhybridized nucleic acid sequence between the probes, and the variant nucleotide resides in that region. Using probes in this manner may prove useful for identification of chromosome translocations, insertions and deletions, and allow sequencing of the adjacent nucleotides.

Applications

By using methods described herein, sequence variations that may cause allelic or phenotypic variation can be identified. In some embodiments genotyping and haplotyping analysis may be performed using at least one, two or more probes and may be carried out in one or more reaction vessels.

Figure 2:
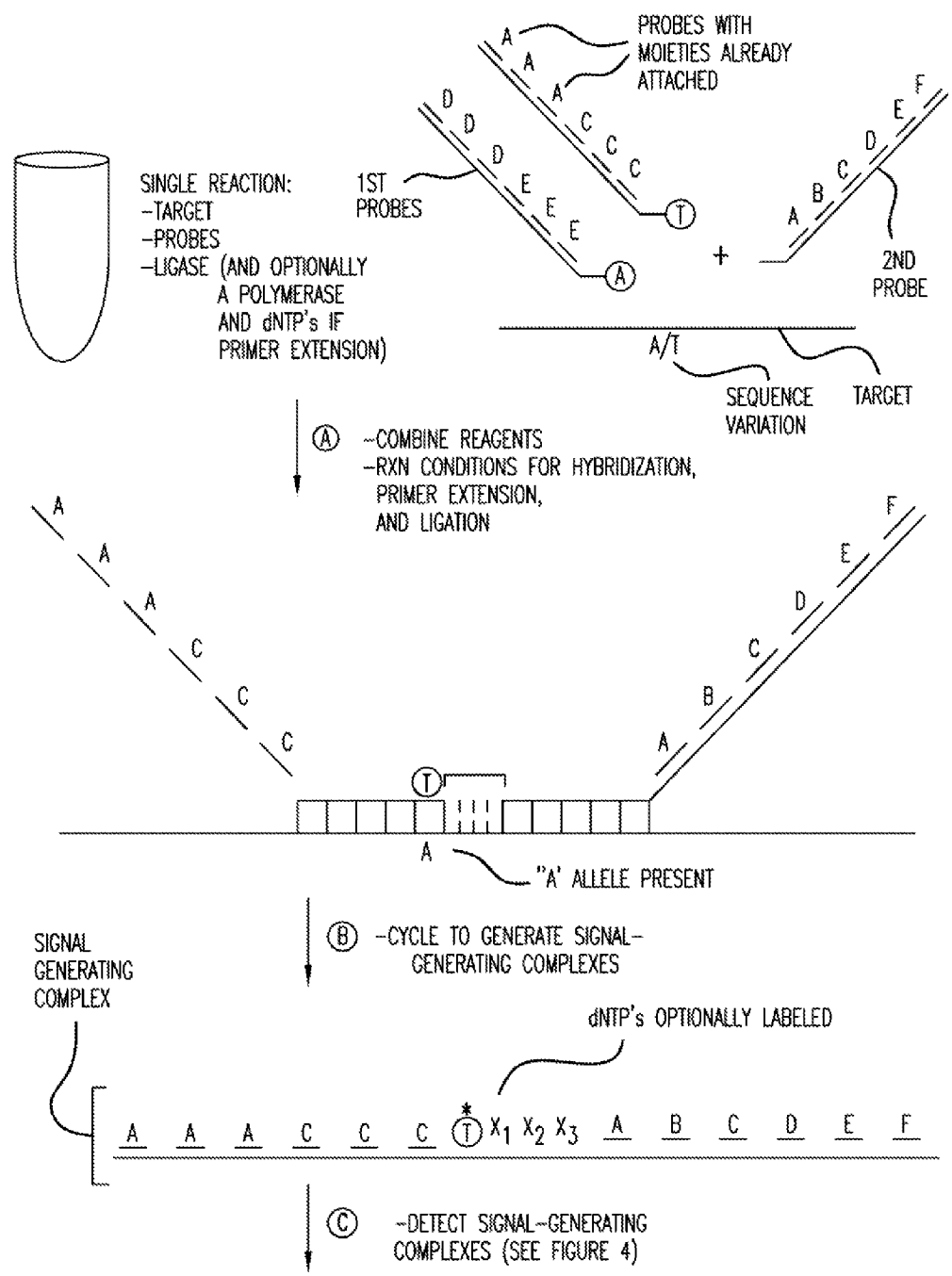
FIGS. 2A-2C depicts a method of determining a sequence variation.
Figure 4:
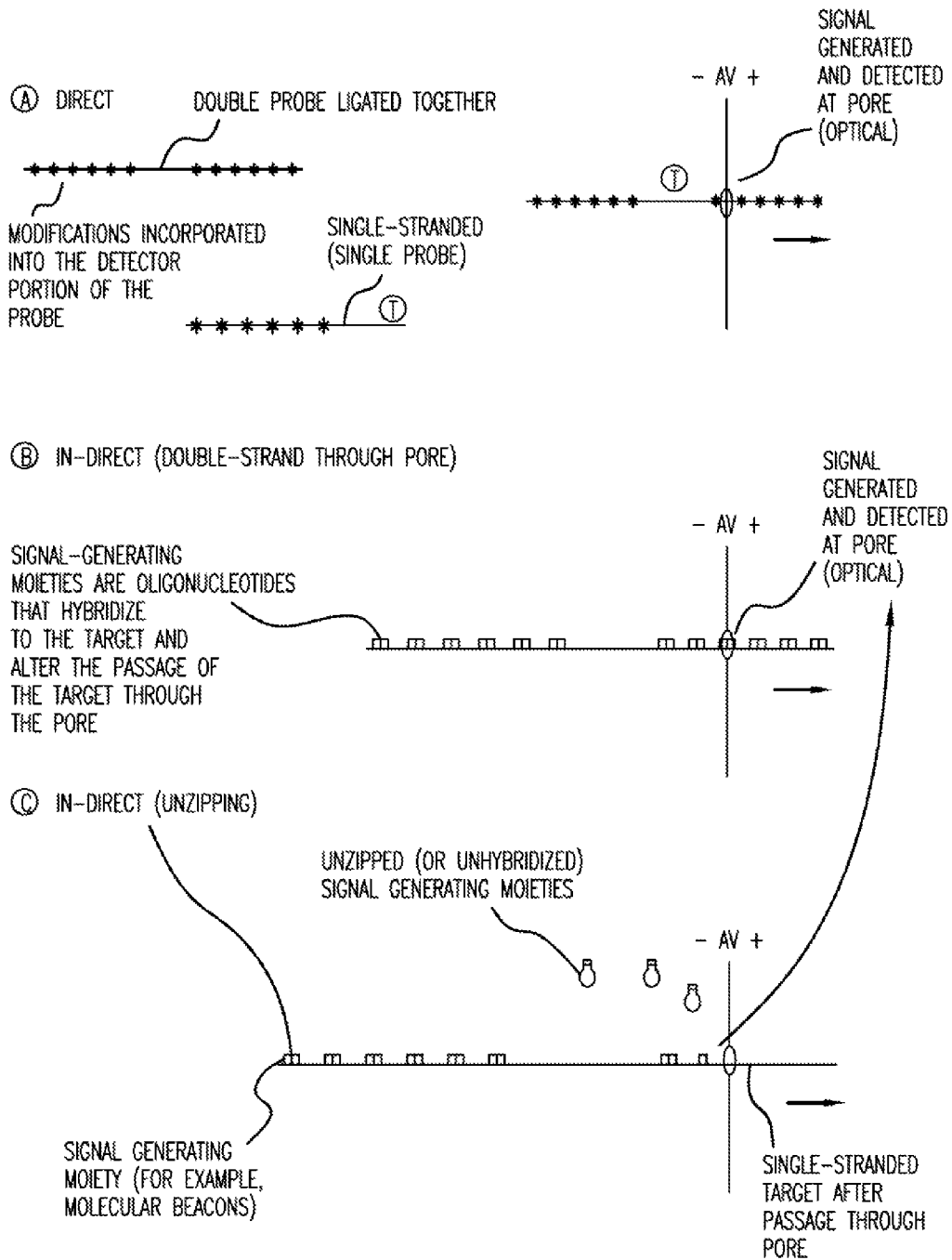
FIG. 4 depicts various signal detection schemes.

Sequence variation determination and sequencing methods can be described generally as (a) hybridization of probe or probes to target nucleic acids (FIG. 2, step A), (b) reaction of probes, target, nucleotides, ligase and/or polymerase to form signal generating complexes (FIG. 2, step A and B), (c) separation of signal generating complexes from target nucleic acid and other unwanted material, and (d) analysis of signal generating complexes, using appropriate means, to identify the nature and location of allelic or phenotypic variation, or nucleotide sequence of the target region (FIG. 2, step C and FIG. 4). Non-limiting examples of types of analysis to which the signal generating complexes may be subjected are, detection of fluorescence, detection of radionuclide incorporation, sequencing, and the like. In some embodiments analysis of signal-generating complexes may be performed by passage of the signal-generating complex through a nanopore, for example in conjunction with sequencing by synthesis methodologies, or for direct measurement of voltage (absolute voltage or voltage differentials) detected at or around the opening of a nanopore. Alterations to these generalized steps will be described in conjunction with specific embodiments for which they are required (e.g., haplotyping using 4 probes and 2 reaction vessels). In some embodiments, a joining reaction may be performed to join the detector portions of probes in proximity to each other, if so desired by the artisan.

Embodiments described herein may be used for genotyping using two separate probes and a single reaction vessel. A first probe and second probe are hybridized with target nucleic acid containing a region of interest (see FIG. 2, step A). The second probe can be hybridized to the target nucleic acid 3' to the first probe. The probes may be hybridized adjacent to a sequence variation. As illustrated in FIG. 2, each probe contains signal-generating moieties that can provide positional and/or sequence information. The probes may be completely unique with respect to each other or may have regions of overlap. A reaction mixture is added to the hybridized probe and target nucleic acid, as illustrated in FIG. 2 step A. In some embodiments the reaction mixture contains ligase, or a ligase, a polymerase and a nucleotide or nucleotides that may be complementary to the sequence variation. The reaction mixture also contains those components necessary for full functionality of added enzymes (e.g., ligase, polymerase). In some embodiments the nucleotide or one of the nucleotides added to the reaction mixture may be optionally labeled. The reaction is allowed to proceed under appropriate reaction conditions (i.e., ligation conditions or polymerase conditions) to form signal-generating complexes (see step B FIG. 2). The resultant nucleic acid complexes may contain the first and second probe ligated together with the target nucleic acid, or the first and second probe ligated together with polymerized nucleotides and the target nucleic acid. Ligases and polymerases are readily available to one of skill in the art, and conditions for use of a particular manufactures product are also readily available.

A signal-generating complex (i.e., the ligated probes or ligated probes with polymerized intervening nucleotides) can then be separated from target nucleic acid, and analyzed. Analysis of a signal-generating complex can provide a signal-generating moiety pattern that, when correlated with location of the first and second probe and analysis of the signal of the nucleotide or nucleotides, determines the nature of the sequence variation, and possibly sequence information of additional adjacent nucleotides (see step C, FIG. 2).

Embodiments described herein may be used for genotyping. In certain embodiments, genotyping methods incorporate the use of two separate probes and two reaction vessels. Steps for genotyping using two probes and two reaction vessels sometimes are substantially the same as those for genotyping using two probes and a single reaction vessel, and differences are outlined herein.

After hybridizing probes and target nucleic acid, a single nucleotide or nucleotides (or possibly a subset of nucleotides) may be added in one reaction vessel, while a different single nucleotide, or nucleotides (or a different subset of nucleotides) may be added to the second reaction vessel, in certain embodiments. The reactions often are processed, in parallel, as described above, and signal generating complexes may be separated and analyzed. Analysis of the signal-generating moiety patterns and correlation with information associated with each signal-generating moiety and determination of whether the complex was formed in the first or second reaction vessel may identify the location and nature of the sequence variation. In some embodiments the steps described above (both general and embodiment specific) may be performed simultaneously and in the same reaction vessel for at least two separate first probes and two separate second probes, wherein each set of first probe and second probe is specific for a separate sequence variation, and provides a signal uniquely indicative of the sequence variation and its location.

Embodiments described herein also may be used for genotyping analysis using one probe and two reactions. Differences in method steps are outlined herein. At least a first probe is hybridized to a target nucleic acid. It will be understood, that many probes may be added as the "at least first probe", wherein only the probe with the correct target-binding portion will hybridize to the target nucleic acid of interest. This may allow the use of large probe libraries in searching for a specific or unique target nucleic acid, to which only a single probe will hybridize. It also may allow analysis of many different target nucleic acids simultaneously. No second probe is added. The hybridized target nucleic acid and first (i.e., only) probe are provided a single nucleotide or nucleotides (or possibly a subset of nucleotides) in one reaction vessel, while a different single nucleotide, or nucleotides (or a different subset of nucleotides) can be added to the second reaction vessel. The reactions are processed, in parallel, as described above. The signal generating complexes may be separated and analyzed. Analysis of the signal-generating moiety patterns and correlation with information associated with each signal-generating moiety and determination of whether the complex was formed in the first or second reaction vessel may identify the location and nature of the sequence variation.

Embodiments described herein also may be used for genotyping analysis using one probe and one reaction. Differences in method steps are outlined herein. At least a first probe is hybridized to a target nucleic acid. All steps after hybridization of a single probe are the same as the steps for genotyping using two probes and one reaction vessel, described above.

Embodiments described herein also may be used for haplotyping analysis using four probes and two reactions. Differences in method steps are outlined herein. At least a first probe is hybridized to a target nucleic acid. A second probe may be hybridized to the target nucleic acid 3' to the first probe. After hybridizing probes and target nucleic acid, a single nucleotide or nucleotides (or possibly a subset of nucleotides) is added in one reaction vessel, while a different single nucleotide, or nucleotides (or a different subset of nucleotides) may be added to the second reaction vessel. The reactions are processed, in parallel, as described above, to generate intermediary signal-generating complexes. At least a third probe may be hybridized to the complexes, at a second 5' portion of the target nucleic acid. A fourth probe can be hybridized to the target nucleic acid 3' of the third probe, where the third and fourth probe may be adjacent to a second sequence variation. A second round of reaction is carried out by providing in the first reaction vessel, a second round of reactants. That is, a second addition of reaction mixture containing ligase, or a ligase, a polymerase and a nucleotide or nucleotides that may be complementary to the sequence variation, and those components necessary for full functionality of added enzymes, is added to the first vessel. A second addition of the reaction mixture is also added to the second vessel. The components are reacted to produce signal-generating complexes.

The complexes generated using this embodiment may comprise complexes formed in the first or second vessel and complexes formed therein may comprise either one of: 1) the ligated first probe, second probe and the target nucleic acid, or 2) the ligated first probe, polymerized nucleotides, second probe and the target nucleic acid; and either one of 3) the ligated third probe and fourth probe, and the target nucleic acid or 4) the ligated third probe, polymerized nucleotides, fourth probe and the target nucleic acid. The signal generating complexes may be separated from target nucleic acid and analyzed. Correlation of the signal generating moiety pattern, identification of which vessel the signal-generating complexes were formed, determination of the nucleotide or nucleotides incorporated between the first and second or third and fourth probe, and the location and sequence information associated with each of the four probes determines the haplotype of the target nucleic acid. In some embodiments the signal-generating complexes may be from the same target nucleic acid.

Embodiments described herein also may be used for haplotyping analysis using four probes and one reaction. Differences in method steps are outlined herein. After the probes are hybridized, as described for haplotyping using 4 probes and two reactions, a reaction mixture containing ligase, or a ligase, a polymerase and a nucleotide or nucleotides that may be complementary to the sequence variation, and those components necessary for full functionality of added enzymes, is added to the hybridized probe and target nucleic acid, and intermediary signal-generating complexes may be formed. The reaction is carried out in a single reaction vessel. A third probe may be hybridized to the intermediary complexes, at a second 5' portion of the target nucleic acid. A fourth probe can be hybridized to the target nucleic acid 3' of the third probe, where the third and fourth probe may be adjacent to a second sequence variation. A second round of reaction is carried out by providing a second round of reactants to the same vessel, and signal-generating complexes are formed. Complexes may be separated from unwanted material and analyzed.

Correlation of the signal generating moiety pattern with the location of the four probes, and analysis of the signal of the labeled nucleotides determines the haplotype of the target nucleic acid.

Embodiments described herein may be used to determine the sequence of a target nucleic acid. The generalized method is presented above. Additional details specific to sequencing embodiments are detailed below. As with the probes described for previous embodiments, the sequencing probes useful for sequencing also have a target binding portion and a detector portion. In order to generate large amounts of sequence information, instead of using one, two, three, or four probes as described for some embodiments above, large numbers of unique probes, or even libraries of unique probes (i.e., unique in both the target binding and the detector portion), may be added to the target nucleic acid during hybridization, as illustrated in FIG. 3. In some embodiments the use of hundreds or even thousands of uniquely informative and identifiable probes may be possible. With careful consideration combinations of probes and detectable labels or moieties greater than 10, 100, 1000, 10,000, 100,000, 1,000,000, or even greater than 10,000,000 possible unique combinations are possible. Non-limiting examples of signal-generating moieties and other detectable labels are presented above, and one of skill in the art can easily choose from other commercially available labels. It will be understood that detectable labels and signal generators not currently available may be adapted to function in embodiments described herein, new fluorophores, or chromophores that may be useable as molecular beacons or function in nanopore applications, for example. It will also be understood that more conventional sequencing reactions may be carried out using the embodiments described herein, using one, two, three, or four sequencing probes or primers.

A reaction mixture, substantially similar to that described above, is added to the target nucleic acid/probe library mixture, as illustrated in FIG. 3, step A. Also illustrated in FIG. 3, step A, are the types of signal-generating complexes that may be formed as a result of carrying out the steps of the sequencing embodiments. Complexes may be formed from ligation of probes directly to each other and target, (i.e., no polymerized nucleotides between the probes, indicating the probes hybridized adjacent and abutting one another) or ligation of probes with intervening polymerized nucleotides and target. The number of nucleotides polymerized between probes may be in the range of about 1 nucleotide to about 500 nucleotides (e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, to about 500 nucleotides).

The complexes (e.g., linked probe molecules) can be separated from unhybridized material and target nucleic acid, thereby forming signal-generating complexes, for example by including a specific tag or affinity binding moiety in the probe. Signal-generating moieties (e.g., molecular beacons) may be added to signal-generating complexes, in some embodiments. The complexes and signal generating moieties are allowed to hybridize, such that signal-generating moieties may bind the ligated probes or ligated probes with polymerized nucleotides. Signal-generating moieties hybridized to the ligated probes or ligated probes and polymerized nucleotides may be analyzed, which includes correlation of the pattern of signal-generating moieties hybridized to each ligated probe complex, and determination of the signal of the labeled nucleotides incorporated during polymerization. The signals can be matched to the respective sequence information associated with each unique signal-generated moiety, and sequences can be assembled to yield the target nucleic acid sequence, as illustrated in FIG. 3 steps C and D. In some embodiments the signal generating moieties may have sequences that may recognize more than one detector portion. For example signal-generating moieties may be designed to recognize short regions of nucleic acid (e.g., about 4 to about 10 nucleotides in length) that may occur more than once in a genome, and therefore may be found in several unique sequencing probes, thus providing a method for relational sequencing (i.e., sequencing by relating nucleotide information associated with a particular nucleotide probe or signal-generating moiety, to a pattern produced by detection of the signal-generating moieties).

Sequencing embodiments described herein can be performed using two probes and one reaction vessel. Differences in method steps are outlined herein. After hybridization of at least a first probe to the 5' portion of the nucleic acid and at least a second probe to the target nucleic acid 3' of the first probe, a reaction mixture is added to the single vessel. The reaction and subsequent preparation of signal generating moieties continues as described above. Analysis of the signal generating moiety pattern and correlation with the specific sequence of the first probe and second probe, the location of the first and second probe, and the signal of the polymerized nucleotides, determines the sequence of the target nucleic acid. In some embodiments using two probes, at least two separate first probes and at least two separate second probes may be used, where each set of probes is specific for a different target nucleic acid, and provides a signal uniquely indicative of the target nucleic acid. In certain embodiments the at least two separate first probes and at least two separate second probes may be designed to hybridize with an entire genome, whereby the sequence of an entire genome can be determined.

Sequencing embodiments described herein can be performed using two separate probes and two reaction vessels. Differences in method steps are outlined herein. After hybridization of at least a first probe to the 5' portion of the nucleic acid and at least a second probe to the target nucleic acid 3' of the first probe, a reaction mixture is added to each of two vessels. The reaction and subsequent preparation of signal generating moieties continues as described above. Analysis of the signal generating moiety pattern and correlation with the specific sequence of the first and second probe, the location of the first and second probe, determination of which reaction vessel the signal generating complex was formed in, and in some embodiments, the signal of the polymerized nucleotides, determines the sequence of the target nucleic acid.

Sequencing embodiments described herein can be performed using one probe and one reaction vessel. Differences in method steps are outlined herein. After hybridization of at least a first probe to the target nucleic acid, where the probe may be adjacent to a base of the target nucleic acid, a reaction mixture is added to the reaction vessel. The reaction and subsequent preparation of signal generating moieties continues as described above. Analysis of the signal generating moiety pattern and correlation with the specific sequence of the probe and analysis of the signal of the nucleotides polymerized determines the sequence of the target nucleic acid.

Sequencing embodiments described herein can be performed using four separate probes and two reaction vessels, to determine the sequence of a larger region of a target nucleic acid. Differences in method steps are outlined herein. After hybridization of at least a first probe to the 5' portion of the nucleic acid and at least a second probe to the target nucleic acid 3' of the first probe, a reaction mixture is added to each of two vessels. The reactions are allowed to proceed, producing intermediary complexes. At least a third probe may be hybridized to the complexes, at a second 5' portion of the target nucleic acid. A fourth probe may be hybridized to the target nucleic acid 3' of the third probe, where the third and fourth probe can be adjacent to a second base of the target nucleic acid. A second round of reaction can be carried out by providing a second round of reactants to the first and second reaction vessels, thereby forming signal-generating complexes. The signal generating complexes may be formed in either the first or second vessel and complexes formed therein may comprise either one of: 1) the ligated first probe, second probe and the target nucleic acid, or 2) the ligated first probe, polymerized nucleotides, second probe and the target nucleic acid; and either one of 3) the ligated third probe and fourth probe, and the target nucleic acid or 4) the ligated third probe, polymerized nucleotides, fourth probe and the target nucleic acid. The signal generating complexes may be separated and analyzed. Correlation of the signal generating moiety pattern, identification of the vessel in which the signal-generating complexes were formed, determination of the nucleotide or nucleotides incorporated between the first and second or third and fourth probe, and the specific sequence information associated with each of the four probes determines the sequence of the nucleic acid target.

Sequencing embodiments described herein can be performed using four separate probes and one reaction vessel, to determine the sequence of a larger region of a target nucleic acid. Differences in method steps are outlined herein. After hybridization of at least a first probe to the 5' portion of the nucleic acid and at least a second probe to the target nucleic acid 3' of the first probe, a reaction mixture is added to the reaction vessel. The reactions are allowed to proceed, producing intermediary complexes. At least a third probe may be hybridized to the complexes, at a second 5' portion of the target nucleic acid. A fourth probe may be hybridized to the target nucleic acid 3' of the third probe, where the third and fourth probe can be adjacent to a second base of the target nucleic acid. A second round of reaction is carried out by providing a second round of reactants to the reaction vessel, thereby producing signal-generating complexes comprising the ligated first probe, labeled nucleotides, second probe, third probe, labeled nucleotides and fourth probe and target nucleic acid. The signal generating complexes may be separated and analyzed. Correlation of the signal generating moiety pattern with the specific base sequence of the four probes, and the signal of the polymerized intervening nucleotides determines the sequence of the target nucleic acid.

Embodiments described herein also may be useful for methylation analysis of target nucleic acids (e.g., methylation-based sequence variation of individual or pooled samples). Methylation analysis using the embodiments described herein follows the general methodology of sequence variation analysis with the added steps of treating a target nucleic acid with an agent to convert non-methylated cytosine to uracil. In methylation-based sequence analysis embodiments, analysis of the signal generating moiety patterns and correlation with probe location, signal of nucleotides incorporated, and in some embodiments determination of which reaction vessel a signal-generating complex was formed in, determines the methylation-based sequence variation. With the exception of the differences outlined herein, methylation-based sequence variation analysis is substantially similar to sequence variation analysis carried out in genotyping embodiments described above, and may be performed using one or two probes in one or two reaction vessels. For example the method for determining a methylation-based sequence variation using two reactions and two probes adds the step of converting non-methylated cytosine to uracil, then follows the method for genotyping sequence variation analysis using two probes and two reactions.

In certain embodiments methylation analysis of pooled samples may be performed using the method of methylation-based sequence variation analysis described above with the following additional steps. Obtaining a first and second pool of nucleic acid containing target nucleic acids for which methylation analysis is desired. The target nucleic acids may be enriched. Nucleic acid enrichment may be by any means available to one of skill in the art that increases the relative abundance of a desired nucleic acid species or target relative to other nucleic acid species, including, but not limited to, PCR amplification, affinity capture and purification (solid or liquid phase), enzymatic treatment (nuclease treatment to remove specific classes of nucleotides, single stranded or double stranded for example), and the like. After enriching the target species, the two pools of target nucleic acids can be treated to convert non-methylated cytosines to uracil. After these initial steps, the method follows that using two probes and two reactions for sequence variation analysis.

In some embodiments the first pool and second pool can originate from the same individual. In certain embodiments the first pool and second pool can originate from different individuals. For example, fetal nucleic acid from maternal serum, plasma or whole blood. In some embodiments the first pool and the second pool may be obtained from the same sample, but represent different fractions obtained from a methylated-nucleic acid-binding-agent column. In some embodiments, quantitative methylation analysis is possible. For example, a difference in degree of methylation between pools can be reflected in the amount of signal generating moiety created. Thus, by analyzing the number of particular signals obtained in each pool over some period of time, a determination can be made regarding the quantitative differences in methylation between pools.

Embodiments described herein may be used to perform methylation analysis using methylated-nucleic acid binding agents. The methodology for performing methylation analysis using methylated-nucleic acid binding agents is similar to methylation based sequence variation analysis with difference outlined herein. Hybridization of at least the first probe may be performed in the presence of a methylated-nucleic acid-binding agent. If the methylation-based sequence variation is a non-methylated sequence variation, the probe will bind, and if it is a methylated sequence variation the probe will not bind. Subsequent steps of the method follow the steps described above for methylation analysis using two probes and two reactions. Correlating the signal generating moiety pattern (i.e., either the presence or absence of signal) with location and sequence of the probes and determination of the vessel in which the signals were formed determines if the methylation-based sequence variation is a non-methylated variation. In some embodiments the methylated-nucleic acid-binding agent may be selected from the group consisting of a protein, an antibody, and a chemical agent. In certain embodiments the binding agent may preferentially bind non-methylated nucleic acids.

Embodiments described herein also may be used to perform quantitative gene expression analysis, and thereby determine and adjust the expression of at least two different target nucleic acid molecules. The steps of the method are described herein. A sample may be prepared by adding a known amount of a first standard nucleic acid having a nucleotide sequence at least one base different than a first target nucleic acid sequence. The nucleotide difference in the two sequences is the point of differentiation between the standard and the sample nucleic acid for later analysis. A reaction mixture suitable for amplification reactions (i.e., PCR amplification, digital PCR, and the like) is added to the prepared sample, and amplification allowed to take place. In some embodiments a limited amplification reaction, also known as pre-amplification, can be performed. Pre-amplification is a method in which a limited amount of amplification occurs due to a small number of cycles, for example 10 cycles, being performed. This allows some amplification, but stops amplification prior to the exponential phase, and typically produces about 500 copies of the desired nucleotide sequence. Use of pre-amplification may also limit inaccuracies associated with depleted reactants in standard PCR reactions, and also may reduce amplification biases due to nucleotide sequence or species abundance of the target.

The term "amplification reaction" as used herein refers to any in vitro means for multiplying the copies of a target sequence of nucleic acid. "Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step. "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Digital PCR is also known to those of skill in the art; see, e.g., US Patent Application Publication Number 20070202525, filed Feb. 2, 2007, which is hereby incorporated by reference.

PCR conditions can be dependent upon primer sequences, target abundance, and the desired amount of amplification, and therefore, one of skill in the art may choose from a number of PCR protocols available (see for example the scientific publications listed above). A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler.

The sample and reactant mixture are allowed to cycle (i.e., amplification occurs), producing additional copies of both the target and standard nucleic acids. The sample containing the amplified standard and target can then subjected to treatment that enhances the difference between the standard and the target nucleic acid. The term "enhancing the difference" as used herein refers to any process that increases the ability to differentiate between the standard and target nucleic acids. Non-limiting examples of enhancement are, methylation, demethylation, addition of affinity capture moiety, capture of one of the two nucleic acid species to a solid support, addition of a detectable label to one but not both nucleic acids, addition of different detectable labels to each nucleic acid, and the like. The amplified products may then be quantified by measuring the ratio of the amplified first target nucleic acid to the amplified first standard nucleic acid to measure the amount of target nucleic acid sequence present in the biological sample. A second standard may be added and the steps of amplification, enhancement and quantification repeated.

A comparison of the quantity of nucleic acids in the first round of amplification and enhancement to the quantity nucleic acids in the second round of amplification and enhancement can be made. If the quantity in the second round of amplification and enhancement is greater than the quantity in the first round, then repeating steps of the first round with a concentration of the first standard and first target nucleic acids which is reduced by the ratio of the quantity of nucleic acids produced in round one over round two, or if the quantity in round one is greater than the quantity in round two, then repeating round two with a concentration of the second standard and second target nucleic acids which is reduced by the ratio of the quantity of nucleic acids produced in round two over the quantity produced in round 1, effectively determines and allows adjustment of the expression of at least two different target nucleic acid molecules.

In amplification embodiments of the invention, an oligonucleotide primer serves as a point of initiation of nucleic acid synthesis. In non-amplification embodiments, an oligonucleotide primer may be used to create a structure that is capable of being cleaved by a cleavage agent. The length and sequences of primers for use in embodiments described herein can be designed based on principles known to those of skill in the art. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides of the invention comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

In certain embodiments, the comparison of methylation states or characteristic methylation states can be made by use of a classification algorithm. In some embodiments, the reagent that modifies unmethylated cytosine to produce uracil may be bisulfite. In certain embodiments, the methylated or unmethylated nucleic acid base is cytosine. In some embodiments, a non-bisulfite reagent can modify unmethylated cytosine to produce uracil.

In some embodiments, the methods for determining the methylation state of (one or more) target gene regions may include treating a target nucleic acid molecule with a reagent that modifies nucleotides of the target nucleic acid molecule as a function of the methylation state of the target nucleic acid molecule, amplifying treated target nucleic acid molecule, fragmenting amplified target nucleic acid molecule, and detecting one or more amplified target nucleic acid molecule fragments, and based upon the fragments, such as size and/or number thereof, identifying the methylation state of a target nucleic acid molecule, or a nucleotide locus in the nucleic acid molecule, or identifying the nucleic acid molecule or a nucleotide locus therein as methylated or unmethylated.

Fragmentation can be performed, for example, by treating amplified products under base specific cleavage conditions. Detection of the fragments can be effected by measuring or detecting a mass of one or more amplified target nucleic acid molecule fragments, for example, by mass spectrometry such as MALDI-TOF mass spectrometry. Detection also can be affected, for example, by comparing the measured mass of one or more target nucleic acid molecule fragments to the measured mass of one or more reference nucleic acid, such as measured mass for fragments of untreated nucleic acid molecules. In an exemplary method, the reagent modifies unmethylated nucleotides, and following modification, the resulting modified target is specifically amplified.

In some embodiments, the methods for determining the methylation state of (one or more) target gene regions may include treating a target nucleic acid molecule with a reagent that modifies a selected nucleotide as a function of the methylation state of the selected nucleotide to produce a different nucleotide; contacting the treated target nucleic acid molecule with a primer containing one or more nucleotides complementary to the selected nucleotide, or one or more nucleotides complementary to the different nucleotide; treating the contacted target nucleic acid molecule under nucleic acid synthesis conditions, whereby nucleotides are synthesized onto primers hybridized to the target nucleic acid molecule; treating the synthesized products under base specific cleavage conditions; and detecting the products of the cleavage treatment, where a target nucleic acid molecule containing one or more methylated or unmethylated selected nucleotides is determined according to the number of cleavage products or according to a comparison between one or more cleavage products and one or more references.

In certain embodiments, the methods for determining the methylation state of (one or more) target gene regions may include treating a target nucleic acid molecule with a reagent that modifies a selected nucleotide as a function of the methylation state of the selected nucleotide to produce a different nucleotide; amplifying the treated target nucleic acid molecule to form an amplification product; contacting the treated target nucleic acid molecule with a primer containing one or more nucleotides complementary to a nucleotide complementary to the selected nucleotide, or one or more nucleotides complementary to a nucleotide complementary to the different nucleotide; treating the contacted target nucleic acid molecule under nucleic acid synthesis conditions, whereby nucleotides are synthesized onto primers hybridized to the target nucleic acid molecule; treating the synthesized products under base specific cleavage conditions; and detecting the products of the cleavage treatment, where a target nucleic acid molecule containing one or more methylated or unmethylated selected nucleotides is determined according to the number of cleavage products or according to a comparison between one or more cleavage products and one or more references.

In some embodiments, the methods for determining the methylation state of (one or more) target gene regions may include treating a target nucleic acid molecule with a reagent selected from among a reagent that modifies an unmethylated selected nucleotide to produce a different nucleotide, and a reagent that modifies a methylated selected nucleotide to produce a different nucleotide; specifically amplifying the treated target nucleic acid molecule by a method selected from: (i) contacting the treated target nucleic acid molecule with a primer that specifically hybridizes to a target nucleic acid region containing one or more of the selected nucleotides or one or more of the different nucleotides, and treating the contacted target nucleic acid molecule under nucleic acid synthesis conditions, and (ii) amplifying the treated target nucleic acid molecule to form an amplification product, contacting the amplification product with a primer that specifically hybridizes to a target nucleic acid region containing one or more of the selected nucleotides, or one or more of the different nucleotides, and treating the contacted amplification product under nucleic acid synthesis conditions; treating the amplified products with base specific cleavage conditions; and detecting the products of the cleavage treatment, where a target nucleic acid molecule containing one or more methylated or unmethylated selected nucleotides may be indicated by an observation selected from among: the presence of two or more cleavage products, the presence of only a single cleavage product, the presence of one or more cleavage products greater than the number of reference nucleic acid molecules, the presence of one or more cleavage products fewer than the number of reference nucleic acid molecules, the presence of the same number of cleavage products as reference nucleic acid molecules, a change in the mass of one or more cleavage products compared to a reference nucleic acid molecule mass, and one or more cleavage products that are the same mass as a reference nucleic acid molecule mass.

In certain embodiments, the methods for determining the methylation state of (one or more) target gene regions may include treating a target nucleic acid molecule with a reagent that modifies unmethylated cytosine to produce uracil; specifically amplifying the treated target nucleic acid molecule with a primer that contains one or more guanine nucleotides; base specifically cleaving the amplified products; and detecting the cleaved products, where the presence of two or more fragments may indicate that the target nucleic acid molecule contains one or more methylated cytosines. Another example includes a method of identifying an unmethylated nucleic acid molecule, by treating a target nucleic acid molecule with a reagent that modifies unmethylated cytosine to produce uracil; specifically amplifying the treated target nucleic acid molecule with a primer that contains one or more adenine nucleotides; base specifically cleaving the amplified products; and detecting the cleaved products, where the presence of two or more fragments may indicate that the target nucleic acid molecule contains one or more unmethylated cytosines.

In some embodiments, the methods for determining the methylation state of (one or more) target gene regions may include treating a target nucleic acid molecule with a reagent that modifies unmethylated cytosine to produce uracil; specifically amplifying the treated target nucleic acid molecule with a primer that contains one or more guanine nucleotides; base specifically cleaving the amplified products; and detecting the mass of the cleaved products, where: a change in mass of one or more cleaved products compared to a reference mass may indicate that a nucleotide locus in a target is methylated. A similar exemplary method includes a method for identifying the nucleotide locus of an unmethylated nucleotide in a nucleic acid, by treating a target nucleic acid molecule with a reagent that modifies unmethylated cytosine to produce uracil; specifically amplifying the treated target nucleic acid molecule with a primer that contains one or more adenine nucleotides; base specifically cleaving the amplified products; and detecting the mass of the cleaved products, where: a change in mass of one or more cleaved products compared to a reference mass may indicate that a nucleotide locus in a target is methylated.

In certain embodiments, methods for determining the methylation state of (one or more) target gene regions may include treating a target nucleic acid molecule to deaminate unmethylated cytosine nucleotides; specifically amplifying the treated target nucleic acid molecule with a primer that specifically hybridizes to a pre-determined first region in a target nucleic acid molecule containing one or more cytosine nucleotides; base specifically cleaving the amplified products; and detecting the mass of the cleaved products, where: a change in mass of one or more cleaved products compared to a reference mass may indicate that a nucleotide locus in a second region in a target is methylated, where the first region and second region do not overlap.

In some embodiments, the methods for determining the methylation state of (one or more) target gene regions may include treating a target nucleic acid molecule with a reagent that modifies unmethylated cytosine to produce uracil; specifically amplifying the treated target nucleic acid molecule with a primer that contains one or more guanine nucleotides; base specifically cleaving the amplified products; and cleaving or simulating cleavage of a reference nucleic acid with the same cleavage reagent(s); detecting the mass of the cleaved products; determining differences in the mass signals between the target nucleic acid molecule fragments and the reference fragments; and determining a reduced set of sequence variation candidates from the differences in the mass signals and thereby determining sequence variations in the target compared to the reference nucleic acid, where methylation of a nucleotide locus can be indicated by the nucleotide locus of a sequence variation.

In another example of the methods, combinations and kits provided herein, a method, combination and kit is provided for identifying the nucleotide locus of a methylated nucleotide in a nucleic acid, by treating a target nucleic acid molecule with a reagent that modifies unmethylated cytosine to produce uracil; amplifying the treated target nucleic acid molecule to form a first amplification product; specifically amplifying the first amplification product with a primer that contains one or more cytosine nucleotides to form a second amplification product; base specifically cleaving the second amplification products; cleaving or simulating cleavage of a reference nucleic acid with the same cleavage reagent(s); detecting the mass of the cleaved products; determining differences in the mass signals between the target nucleic acid molecule fragments and the reference fragments; and determining a reduced set of sequence variation candidates from the differences in the mass signals and thereby determining sequence variations in the target compared to the reference nucleic acid, where methylation of a nucleotide locus may be indicated by the nucleotide locus of a sequence variation.

In certain embodiments, the methods for determining the methylation state of (one or more) target gene regions may include treating two or more different target nucleic acid molecules with a reagent that modifies a selected nucleotide as a function of the methylation state of the selected nucleotide to produce a different nucleotide; contacting the treated target nucleic acid molecules with a primer containing one or more nucleotides complementary to the selected nucleotide, or one or more nucleotides complementary to the different nucleotide; treating the contacted target nucleic acid molecules under nucleic acid synthesis conditions, whereby nucleotides are synthesized onto primers hybridized to the target nucleic acid molecules; treating the synthesized products under base specific cleavage conditions; and detecting the products of the cleavage treatment, where target nucleic acid molecules containing one or more methylated or unmethylated selected nucleotides can be determined according to a comparison between one or more cleavage products and one or more references.

In some embodiments, the methods for determining the methylation state of (one or more) target gene regions may include treating a target nucleic acid molecule with a reagent that modifies a selected nucleotide as a function of the methylation state of the selected nucleotide to produce a different nucleotide; contacting the treated target nucleic acid molecule with a primer containing one or more nucleotides complementary to the selected nucleotide, or one or more nucleotides complementary to the different nucleotide; treating the contacted target nucleic acid molecule under nucleic acid synthesis conditions, whereby nucleotides are synthesized onto primers hybridized to the target nucleic acid molecules; treating the synthesized products under fragmentation conditions; and detecting the products of the fragmentation treatment by mass spectrometry, where target nucleic acid molecules containing one or more methylated or unmethylated selected nucleotides can be determined according to the number of fragmentation products or according to a comparison between one or more fragmentation products and one or more references.

Similarly, methods are provided for identifying one or more methylated or unmethylated nucleotides in a nucleic acid, by treating a target nucleic acid molecule with a reagent that modifies a selected nucleotide as a function of the methylation state of the selected nucleotide to produce a different nucleotide; contacting the treated target nucleic acid molecule with a blocking oligonucleotide containing one or more nucleotides complementary to the selected nucleotide, or one or more nucleotides complementary to the different nucleotide; treating the contacted target nucleic acid molecule under nucleic acid synthesis conditions, where nucleotide synthesis is inhibited when the blocking oligonucleotide is hybridized to a target nucleic acid molecule; treating the synthesized products under base specific cleavage conditions; and detecting the products of the cleavage treatment, where a target nucleic acid molecule containing one or more methylated or unmethylated selected nucleotides can be determined according to the number of cleavage products or according to a comparison between one or more cleavage products and one or more references.

In certain embodiments, the methods for determining the methylation state of (one or more) target gene regions may include treating a target nucleic acid molecule with a reagent that modifies a selected nucleotide as a function of the methylation state of the selected nucleotide to produce a different nucleotide; contacting the target nucleic acid molecule with a cleavage reagent that selectively cleaves the target nucleic acid at a site containing one or more methylated selected nucleotides or one or more unmethylated selected nucleotides, or with a cleavage reagent that selectively cleaves the treated target nucleic acid at a site containing one or more selected nucleotides or one or more different nucleotides; treating the contacted target nucleic acid molecule under nucleic acid synthesis conditions, where a target nucleic acid molecule not cleaved is amplified; treating the amplified products under base specific cleavage conditions; and detecting the products of the cleavage treatment, where a target nucleic acid molecule containing one or more methylated or unmethylated selected nucleotides can be determined according to the number of cleavage products or according to a comparison between one or more cleavage products and one or more references.

In some embodiments, the methods for determining the methylation state of (one or more) target gene regions may include contacting the target nucleic acid molecule with a primer and treating the contacted target nucleic acid molecule under nucleic acid synthesis conditions, where a strand complementary to the target nucleic acid molecule can be synthesized; contacting the target nucleic acid-synthesized product duplex with a methyltransferase reagent whereby methylation in a CpG sequence of the target nucleic acid also is present in the complementary CpG sequence of the synthesized product; repeating the primer and methyltransferase reagent contacting steps to form a second synthesized product having the same sequence of nucleotides and methylation state of CpG nucleotides as present in the target nucleic acid molecule; treating synthesized products with a reagent that modifies a selected nucleotide as a function of the methylation state of the selected nucleotide to produce a different nucleotide; treating the reagent-treated products under base specific cleavage conditions; and detecting the products of the cleavage treatment, where a target nucleic acid molecule containing one or more methylated or unmethylated selected nucleotides can be determined according to the number of cleavage products or according to a comparison between one or more cleavage products and one or more references.

In certain embodiments, the methods for determining the methylation state of (one or more) target gene regions may include identifying one or more methylated or unmethylated nucleotides in a nucleic acid, where the amplified products can be cleaved by base specific cleavage conditions selected from chemical conditions, physical conditions, enzymatic base specific cleavage conditions, and combinations thereof. For example, the amplified products can be cleaved by an RNase, a DNase, an alkaline compound, piperidine formate, piperidine, dimethyl sulfate, hydrazine, sodium chloride, and combinations thereof.

In some embodiments, the methods for determining the methylation state of (one or more) target gene regions may include identifying one or more methylated or unmethylated nucleotides in a nucleic acid, where the amplifying step includes transcription. In such methods, the nucleoside triphosphates incorporated into the transcript can include three rNTPs and one dNTP. For example, the one dNTP can be selected from dCTP, dTTP, dATP and dGTP. In another example, the one dNTP can be selected from dCTP and dTTP, and the transcript can be cleaved by RNase A.

In certain embodiments, the methods for determining the methylation state of (one or more) target gene regions may include identifying one or more methylated or unmethylated nucleotides in a nucleic acid, where the intensity of one or more measured sample masses can be compared to the intensity of one or more reference masses. Similarly, also provided herein are methods of identifying one or more methylated or unmethylated nucleotides in a nucleic acid, where two or more nucleic acid samples are pooled, and the intensity of one or more measure sample masses can be compared to the intensity of one or more reference masses. In such methods an incompletely converted target nucleic acid molecule can be distinguished from a methylated target nucleic acid molecule.

In some embodiments, the methods for determining the methylation state of (one or more) target gene regions may be used for distinguishing between a false positive methylation specific amplification and a true methylation specific amplification, by, for example, treating a target nucleic acid molecule with a reagent that modifies an unmethylated selected nucleotide to produce a different nucleotide; contacting the treated target nucleic acid molecule with a methylation state specific primer complementary to a first target nucleic acid region containing one or more of the selected nucleotides; treating the contacted target nucleic acid molecule under nucleic acid synthesis conditions; treating the synthesized products under base specific cleavage conditions; and detecting the mass of the cleaved products, where: a change in mass of one or more cleaved products compared to a reference mass may indicate that a nucleotide locus in a second region in a target is methylated, where the second region does not overlap with the first region, whereby presence of one or more methylated loci in the second region confirms true methylation specific amplification.

In certain embodiments, the methods for determining the methylation state of (one or more) target gene regions may be used for identifying methylated nucleotides and thereby identify methylation patterns, which can be correlated with a disease, disease outcome, or outcome of a treatment regimen, by, for example, identifying methylated or unmethylated nucleotides, in accordance with the method of any of methods provided herein, in one or more nucleic acid molecules from one or more samples collected from one or more subjects having a known disease, disease outcome, or outcome of a treatment regimen; identifying methylated or unmethylated nucleotides, in accordance with the method of any of methods provided herein, in one or more nucleic acid molecules from one or more samples collected from one or more normal subjects; and identifying the differently methylated or unmethylated nucleotides between the one or more nucleic acid molecules of step (a) and the one or more nucleic acid molecules of step (b); whereby the differently methylated or unmethylated nucleotides may identify methylation correlated with a disease, disease outcome, or outcome of a treatment regimen.

In some embodiments, the methods for determining the methylation state of (one or more) target gene regions may be used for determining the probable identity of one or more alleles, by, for example, identifying one or more methylated or unmethylated nucleotides a nucleic acid molecule; and determining the frequency of presence of one or more alleles with the presence of one or more methylated or unmethylated nucleotides where the probable identity of the allele can be determined.

Also provided herein are combinations and kits for determining the methylation state of a target nucleic acid molecule. Kits can include a reagent that modifies one or more nucleotides of the target nucleic acid molecule as a function of the methylation state of the target nucleic acid molecule, one or more methylation specific primers capable of specifically hybridizing to a treated target nucleic acid molecule, and one or more compounds capable of fragmenting an amplified target nucleic acid molecule. The one or more compounds capable of fragmenting amplified nucleic acid products can include an RNase, a DNase, an alkaline compound, piperidine formate, piperidine, dimethyl sulfate, hydrazine, sodium chloride, and combinations thereof. For example, kits provided herein can include one or more RNases In some embodiments, the methylation state can be determined by use of a nanopore. In some embodiments, the methylation state can be determined by multiplexed hME assays, fluorescence-based real-time PCR, methylation-sensitive single nucleotide primer extension, methylated CpG island amplification, methylation-specific PCR, restriction landmark genomic scanning, methylation-sensitive-representational difference analysis (MS-RDA), methylation-specific AP-PCR (MS-AP-PCR) methyl-CpG binding domain column/segregation of partly melted molecules (MBD/SPM), or bisulphite sequencing direct. Specific methods for determining the methylation state may include combined bisulfite restriction analysis (COBRA), PyroMeth or MethyLight.

Platforms and Analytical Processes

Certain process embodiments described herein give rise to signal-generating complexes that can be analyzed to elucidate nucleic acid sequence information. Non-limiting examples of types of sequence information that can be determined using methods described herein are nucleotide sequences, presence or absence of a sequence, relative or absolute copy number of a sequence, or methylation status. In some embodiments signal generating moieties may be contacted with a nanopore device to generate a signal generating moiety pattern. A signal generating moiety pattern can be analyzed and correlated with information associated with detector portions of the probes, and in some embodiments, within the specific reaction vessel in which the signal-generating complexes were formed.

Advances in nucleic acid analysis technology have included the use of nanopore technology to determine, for example, the sequence of a nucleic acid. A nanopore is a hole on the order of 1 nanometer in internal diameter in either a piece of silicon or naturally occurring as a transmembrane protein. In some embodiments, a nanopore maybe larger than 1 nanometer, and may be about 1 nanometer, 2, 3, 4, 5, 6, 7, 8, 9, 10, 20, 30, 40, 50, 60, 70, 80, 90, or up to 100 nanometers in size. When a nanopore is immersed in a conducting fluid and a voltage is applied, an electric current due to conduction of ions through the nanopore is observed. The amount of current is sensitive to the size of the nanopore. FIG. 4A-4C illustrates various aspects of nanopore devices including direct and indirect detection methods. As used herein, for nanopore based detection, "direct and indirect methods" refers to either a direct reading of the nucleic acid sequence, or an indirect reading of the nucleic acid sequence by the detection of a signal moiety that gives off a detectable signal at or around the nanopore opening, as in some sequencing by synthesis methods. In some embodiments a nanopore device may be used to determine a nucleic acid sequence in conjunction with sequencing by synthesis protocols, and direct or indirect detection methods.

FIG. 4A is a line diagram of certain aspects of a nanopore device associated with detecting changes in electrical voltage or ion flow at or around the opening of a nanopore. The vertical line, with an opening in the middle, to the right of panel FIG. 4A, represents the nanopore device and denotes a separation between two spaces (e.g., left and right spaces, inner and outer spaces, or two chambers, as non-limiting examples). That is, a physical barrier exists between the two sides of the vertical line, which inhibits the free passage of material from one side to the other. This barrier allows the formation of a gradient (electrical, magnetic or chemical) as denoted above the vertical line, by the (−) and (+) signs on either side of the "delta" V symbol (i.e., the triangle traditionally associated with the term "change" in chemical and biological formulas, or mathematical equations), where "V" is the commonly accepted symbol for voltage. The separation of the (−) and (+) indicate that a gradient is formed on either side of the vertical line representing the nanopore device, which can cause a current to be formed, which in turn may cause a directed flow of sample through the nanopore opening.

In FIG. 4A, signal generating complexes are represented by horizontal lines with asterixes (*), which denote detectable label. The label can be incorporated during synthesis or added post-synthetically. Non-limiting examples of detectable labels are described above. In FIG. 4A, three types of signal-generating complexes are shown, (1) a signal generating complex formed by joining a pair of probes from a probe set that hybridized to a target nucleic acid adjacent to one another, and with no intervening sequences (i.e., they abut one another), described as "double probe ligated together", (2) a signal-generating complex described as "single-stranded probe (single-probe)", which includes an incorporated nucleotide (T), but no additional probe of a probe set is ligated or joined (as might be the case in methylation studies or single probe haplotyping studies), and (3) a signal generating complex formed by the incorporation of a nucleotide (T) as well as ligation of two adjacent probes, illustrated as passing through the pore.

In some embodiments a change in current due to conduction of ions through a blocked or partially blocked pore, can be measured at or around the pore, as illustrated in FIG. 4A. As nucleic acid molecules pass through a nanopore, the nucleic acid may cause a partial blockage that may change the magnitude of the current, which passes through the nanopore. The change in ion flow, current, or other electrical property (nucleotide charge (e.g. nucleotide with added charges), charge associated with a detectable moiety) may be measured by direct measurement of the change in voltage or current by use of devices that measure such electrical, ionic, or gradient changes, such as a patch clamp for example, or other suitable measurement devices. In some embodiments detection of the labeled moiety at or around the pore opening also may be accomplished by direct measurement of radioactive decay, light scattering, fluorescence, and the like, from the nucleic acid as it passes through the pore, using suitable detection devices.

In some embodiments detection of the identity of the nucleotide flowing through a nanopore at any given moment also may be possible due to the differences in the dimensions of each nucleotide, as the nucleic acid is passed through the nanopore. The change in the current through the nanopore as a nucleic acid molecule passes through the nanopore represents a direct reading of the DNA sequence. One such method of single nucleotide sequencing using a nanopore device is described in U.S. Provisional Patent Application Ser. No. 61/021,872 filed Jan. 17, 2008, and incorporated herein by reference, in its entirety. In some embodiments, nucleotides that are size modified may be used in order to facilitate detection and determination.

In some embodiments a nanopore device can be used to detect signal generating moiety patterns of double stranded nucleic acid signal-generating complexes, as illustrated in FIG. 4B. In FIG. 4B aspects of the nanopore device are substantially similar to those described above. The signal-generating complex in FIG. 4B is a target nucleic acid (either a ligated probe, joined probe, or sample nucleic acid), to which a detector moiety is hybridized (e.g., molecular beacon). This embodiment is an example of an indirect method of detection, as information about the nucleotide sequence is determined by detection of a hybridized "beacon". The moiety may be associated with a certain nucleotide repeat, or other sequence, and in the embodiment illustrated in FIG. 4B occurs repeatedly. Detection of the signal-generating moiety, and in some embodiments the regularity of occurrence of the signal generating moiety, can be determined by measuring the time interval associated with the appearance of the detectable moiety at or around the nanopore opening, and correlating that information with the rate of nucleotide movement through the nanopore. For example, if a substantially double stranded signal-generating complex passed through the opening of a nanopore at 10 base pairs (bp) per second, and a particular detectable moiety passed through the opening every 10 seconds, the estimated distance between each repeating signal is about 100 base pairs. The term "substantially double stranded" refers to double-stranded nucleic acids, either naturally occurring or the product of molecular manipulation (for example, a probe and/or non-specific nucleic acid (sheared calf thymus DNA) hybridized to a target nucleic acid), where greater than 55%, 60%, 65%, 70%, 75%, 80%, 85%, 90%, 95% or greater than 99% of the nucleic acid is double stranded. Baseline measurements of the rate of passage of nucleic acids of differing percent double strandedness may be made to allow flexibility of experimental design, as well as system calibration.

In some embodiments, a plurality of differentially labeled molecular beacons, each with a unique detectable moiety, may be hybridized to a target nucleic acid and ligated or joined to form a signal generating complex and a "map" or pattern of moiety positions generated based on the number of times each particular moiety passed through the nanopore, the spacing between each passage event, or a combination thereof. In some embodiments, a single labeled beacon may be used and the target nucleic acid made substantially double stranded by hybridization of non-detectable nucleic acid.

Illustrated in FIG. 4C is another indirect method of sequence determination by moiety detection where, molecular beacons or other detectable moieties are unzipped or removed from a double stranded target sequence by a protein nanopore (e.g. α-hemolysin), and the act of unzipping controls the rate of nucleic acid translocation (i.e., passage) through the nanopore (Soni and Meller, Progress toward Ultrafast DNA sequencing using Solid-State Nanopores, Clinical Chemistry 53(11):1996-2001 2007, incorporated herein in its entirety). In embodiments using this detection method, probes representing a binary conversion of the nucleic acid sequence, and designed as molecular beacons are hybridized to a target nucleic acid. The binary conversion of the sequence simplifies reading the nucleic acid sequence, and the unzipping of the bound sequence at the pore controls the rate of passage, thus controlling both the speed and contrast of the detection and allowing more accurate sequence determination. Detection occurs at or around the nanopore during or just prior to unzipping. In some embodiments, detection occurs at a location removed from the pore, and the pore controls the rate of passage of nucleotides past the detector by unzipping the beacons, thereby slowing the passage sufficiently to allow both increased resolution and more accurate detection.

Single nucleotide sequencing methodologies that also are useful with nanopore devices and which may be used in embodiments described herein, include pyrosequencing. Pyro-sequencing is a method of DNA sequencing by synthesis. Sequencing by synthesis involves taking a single strand of DNA and synthesizing the complimentary strand enzymatically in a reaction, which is coupled to a chemiluminescent enzyme. In pyrosequencing embodiments, successful incorporation of a base liberates a pyrophosphate (PPi), which is converted into ATP, which then produces visible light through a reaction with luciferin. A camera detects the production of the visible light. The amount of light liberated is proportional to the amount of ATP produced. A number of pyro-sequencing methods and devices are available to the artisan, including, by way of non-limiting example, the Genome Sequencer FLX with GS FLX Titanium series reagents by 454 Life Sciences, a Roche company (Branford, Conn.).

In some embodiments target nucleic acid species also can be further analyzed by the nucleotide sequencing methods described below, although any suitable sequencing method can be utilized. In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008, and incorporated herein by reference, in its entirety.

Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni GV and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allow sequencing of clonally expanded or non-amplified single molecules of nucleic acid fragments.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the dectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

Examples of Embodiments

Presented hereafter are specific, and non-limiting, embodiments of the invention.

Provided in part is a method for genotyping which incorporates the use of two separate reactions and two separate probes (i.e. a probe pair) for determining a sequence variation of a target nucleic acid molecule comprising the steps of: (a) hybridizing at least a first probe to the 5' portion of a target nucleic acid; (b) hybridizing a second probe to the target nucleic acid 3' of the first probe where the first and second probes may be adjacent to a sequence variation and define a region there between, where the region between the probes may comprise either no nucleotides, one nucleotide or more than one nucleotide; (c) providing in a first reaction vessel a ligase or a ligase, a polymerase and a first nucleotide or nucleotides, the first nucleotide or nucleotides which may be complementary to a sequence variation and ligating together the first probe and second probe if the probes are complementary to the target nucleic acid or polymerizing the nucleotide(s) and ligating together the first probe and second probe and nucleotides(s) if the nucleotide(s) is complementary to the sequence variation; (d) providing in at least a second reaction vessel a ligase or a ligase, a polymerase and a second nucleotide or nucleotides, the nucleotide or nucleotides which may be complementary to the sequence variation and ligating together the first probe and second probe if the probes and nucleotide(s) are complementary to the target nucleic acid or polymerizing the nucleotides and ligating together the first probe and second probe and nucleotide(s) if the nucleotide(s) is complementary to the sequence variation, whereby a complex comprising either the ligated first probe and second probe, and target nucleic acid or the ligated first probe and polymerized nucleotides and second probe, and target nucleic acid, is formed; (e) separating the complex formed as the result of step (c), step (d), or a combination thereof, from the target nucleic acid to form a signal-generating complex; and (f) performing an analysis of the signal-generating complex of step (e) to provide a signal-generating moiety pattern and where correlation of the signal-generating moiety pattern with the location of the first and the second probe, and determination of whether the complex of step (e) has been formed in the first or the second reaction vessel or the first and the second reaction vessel determines the sequence variation.

In certain embodiments that use two separate reactions and two separate probes for determining a sequence variation of a target nucleic acid molecule, the analysis in step (f) may be performed by passing a signal-generating complex through a nanopore. In some embodiments, a first probe further comprises a target binding portion and a detectable portion that provides a signal informative as to the probes location within the target, and further where the detectable portion does not hybridize to the target nucleic acid, and the detectable portions composition may be independent of the sequence of the target nucleic acid. In certain embodiments a second probe further comprises a target binding portion and a detectable portion that provides a signal informative as to the probes location within the target, and further where the signal generating moiety does not hybridize to the target nucleic acid, and its composition may be independent of the sequence of the target nucleic acid. In some embodiments a signal-generating complex comprises one or more signal-generating moieties that may be integral to the signal-generating complex. In certain embodiments a signal-generating complex may comprise single-stranded nucleic acid and the one or more signal-generating moieties can be labeled nucleotides. In some embodiments a signal-generating complex comprises one or more signal-generating moieties that can be hybridized to the signal-generating complex.

In some embodiments a signal-generating moiety hybridized to a signal-generating complex cam be a molecular beacon. In certain embodiments a first probe is complementary to a target nucleic acid at a sequence variation. In certain embodiments at least two first probes are introduced to the reaction vessel of step (c), and in step (a) only the first probe that is complementary to the sequence variation hybridizes to the target nucleic acid. In certain embodiments, multiplexing of the methods disclosed herein may be performed; for example, each of steps (a)-(e) may be performed in at least two or more reaction vessels for at least two separate first probes and two separate second probes, where each set of first probe and second probe can be specific for a separate sequence variation, and provides a signal uniquely indicative of a specific sequence variation and its location. A set of first probes and second probes may constitute a set of probes sufficient to provide information about the sequence variations of an entire genome, in some embodiments.

Also provided, in part, is a method for genotyping which uses one reaction and two separate probes for determining a sequence variation of a target nucleic acid molecule comprising the steps of: (a) hybridizing at least a first probe to the 5' portion of a target nucleic acid; (b) hybridizing a second probe to the target nucleic acid 3' of the first probe where the first and second probes may be adjacent to a sequence variation, and define a region there between, where the region between the probes may comprise either no nucleotides, one nucleotide or more than one nucleotide; (c) providing in a reaction vessel a ligase or a ligase, a polymerase and a labeled nucleotide or nucleotides, the nucleotide or nucleotides which may be complementary to the sequence variation and ligating together the first probe and second probe if the probes are complementary to the target nucleic acid or polymerizing nucleotides and ligating together the first probe and second probe and nucleotide(s) if the nucleotide(s) is complementary to the sequence variation, whereby a complex comprising either the ligated first probe and second probe and target nucleic acid or the ligated first probe and polymerized nucleotides and second probe and target nucleic acid is formed; (d) separating the complex of step (c) from the target nucleic acid to form a signal-generating complex; and (e) performing an analysis of the signal-generating complex of step (d) to provide a signal generating moiety pattern and where correlation of the signal generating moiety pattern with the location of the first and the second probe, and analysis of the signal of the nucleotide determines the sequence variation.

In some embodiments that use one reaction and two separate probes for determining a sequence variation of a target nucleic acid molecule, the analysis in step (e) of a signal-generating complex may be performed by passage of the signal-generating complex through a nanopore. In certain embodiments the labeled nucleotide may be labeled with an affinity capture moiety. In some embodiments that use one reaction and two separate probes for determining a sequence variation, each of steps (a)-(d) may be performed simultaneously and in the same reaction vessel for at least two separate first probes and two separate second probes, where each set of first probe and second probe can be specific for a separate sequence variation, and provides a signal uniquely indicative of a specific sequence variation and its location.

Also provided, in part, is a method for genotyping which uses two reactions and one probe for determining a sequence variation of a target nucleic acid molecule comprising the steps of: (a) hybridizing at least a first probe to a portion of a target nucleic acid, where the probe may be adjacent to a sequence variation; (b) providing in a first reaction vessel a polymerase and a first nucleotide or nucleotides, the nucleotide or nucleotides which may be complementary to a sequence variation and extending the probe with the nucleotide(s) if the nucleotide(s) is complementary to the sequence variation; (c) providing in at least a second reaction vessel a polymerase and a second nucleotide or nucleotides which may be complementary to the sequence variation and extending the probe with nucleotide(s) if the nucleotide(s) is complementary to the sequence variation, whereby a complex comprising the extended probe and nucleotide(s), and target nucleic acid is formed; (d) separating the complex formed as the result of step (b), step (c), or a combination thereof, from the target nucleic acid to form a signal-generating complex; and (e) performing an analysis of the signal-generating complex of step (d) to provide a signal generating moiety pattern and where correlation of the signal generating moiety pattern with the location of the first probe, and determination of whether the complex of step (d) has been formed in the first or the second reaction vessel or the first and the second reaction vessel determines the sequence variation.

In some embodiments the probe further comprises a target binding portion and a detectable portion and which provides a signal informative as to the probes location within the target nucleic acid, and further where the detectable portion does not hybridize to the target nucleic acid, and the probes composition may be independent of the sequence of the target nucleic acid. In certain embodiments using two reactions and one probe for determining a sequence variation of a target nucleic acid molecule, the analysis in step (e), of a signal-generating complex, may be performed by passage of the signal-generating complex through a nanopore Also provided, in part, is a method for genotyping which uses one reaction and one probe for determining a sequence variation of a target nucleic acid molecule comprising the steps of: (a) hybridizing at least a first probe to a portion of the target nucleic acid, where the probe may be adjacent to the sequence variation; (b) providing in a reaction vessel a polymerase and a labeled nucleotide or nucleotides which may be complementary to a sequence variation and extending the probe with the nucleotide(s) if the nucleotide(s) is complementary to the sequence variation, whereby a complex comprising the extended probe and nucleotide(s), and target nucleic acid is formed; (c) separating the complex of step (b) from the target nucleic acid to form a signal-generating complex; and (d) performing an analysis of the signal-generating complex of step (c) to provide a signal generating moiety pattern and where correlation of the signal generating moiety pattern with the location of the first probe, and analysis of the signal of the nucleotide determines the sequence variation. In certain embodiments using one reaction and one probe for determining a sequence variation of a target nucleic acid molecule, the analysis in step (d) of a signal-generating complex may be performed by passage of the signal-generating complex through a nanopore.

Also provided, in part, is a method for haplotyping that uses two reactions and four separate probes for determining the haplotype of a target nucleic acid molecule comprising the steps of: (a) hybridizing at least a first probe to the 5' portion of a target nucleic acid; (b) hybridizing a second probe to the target nucleic acid 3' of the first probe where the first and second probes may be adjacent to a first sequence variation of the target nucleic acid sequence, and define a region there between, where the region between the probes may comprise either no nucleotides, one nucleotide or more than one nucleotide; (c) providing in a first reaction vessel a ligase or a ligase, a polymerase and a first nucleotide or nucleotides, the nucleotide or nucleotides which may be complementary to a first sequence variation and ligating together the first probe and second probe if the probes are complementary to the target nucleic acid or polymerizing the nucleotides and ligating together the first probe, the second probe and the nucleotide(s) if the nucleotide(s) is complementary to the first sequence variation; (d) providing in at least a second reaction vessel a ligase or a ligase, a polymerase and a second nucleotide or nucleotides, the nucleotide or nucleotides which may be complementary to the sequence variation and ligating together the first probe and second probe if the probes are complementary to the target nucleic acid or polymerizing the nucleotides and ligating together the first probe, the second probe and the nucleotide(s) if the nucleotide(s) is complementary to the first sequence variation; (e) hybridizing at least a third probe to a second 5' portion of the target nucleic acid; (f) hybridizing a fourth probe to the target nucleic acid 3' of the third probe where the third and fourth probes are adjacent to a second sequence variation of the target nucleic acid sequence and define a region there between, the region between the probes may comprise either no nucleotides, one nucleotide or more than one nucleotide and further where the 3' portion of the third probe and the 5' portion of the fourth probe may be ligated to each other; (g) providing in the first reaction vessel a ligase or a ligase, a polymerase and a first nucleotide or nucleotides, the nucleotide or nucleotides which may be complementary to the second sequence variation and ligating together the third probe and fourth probe if the probes are complementary to the target nucleic acid or polymerizing the nucleotides and ligating together the third probe and fourth probe and nucleotide(s) if the nucleotide(s) is complementary to the second sequence variation; (h) providing in the at least second reaction vessel a ligase or a ligase, a polymerase and a second nucleotide or nucleotides, the nucleotide or nucleotides which may be complementary to the sequence variation and ligating together the third probe and fourth probe if the probes are complementary to the target nucleic acid or polymerizing the nucleotides and ligating together the third probe and fourth probe and nucleotide(s) if the nucleotide(s) is complementary to the second sequence variation, whereby a complex comprising either one of: 1) the ligated first probe and second probe of step (c), and the target nucleic acid or 2) the ligated first probe, polymerized nucleotides, second probe of step (c), and the target nucleic acid; and either one of 3) the ligated third probe and fourth probe of step (g), and the target nucleic acid or 4) the ligated third probe, polymerized nucleotides, fourth probe of step (g) and the target nucleic acid is formed or a complex comprising either one of: 1) the ligated first probe and second probe of step (d), and the target nucleic acid or 2) the ligated first probe, polymerized nucleotides, second probe of step (d), and target nucleic acid; and either one of 3) the ligated third probe and fourth probe of step (h), and the target nucleic acid or 4) the ligated third probe, polymerized nucleotides, fourth probe of step (h) and target nucleic acid is formed; (i) separating any of the complexes of step m) from the target nucleic acid to form a signal-generating complex; and (j) performing an analysis of the signal-generating complex of step (i) to provide a signal generating moiety pattern and where correlation of the signal generating moiety pattern with the location of the first, second, third and fourth probe, and determination of whether the signal-generating complex of step (i) has been formed in the first or the second reaction vessel or the first and the second reaction vessel thereby identifying either the reaction in which ligation occurred or the nucleotide or nucleotides ligated between the first and second and third and fourth probes determines the haplotype of the target nucleic acid.

In certain embodiments using two reactions and four separate probes for determining the haplotype of a target nucleic acid molecule the analysis in step (j) of any of the signal-generating complexes of step (i) may be performed by passage of any of the signal-generating complexes through a nanopore. In certain embodiments the first probe further comprises a target binding portion and a detectable portion which provides a signal informative as to the probes location within the target nucleic acid, and further where the detectable portion does not hybridize to the target nucleic acid, and the detectable portions composition may be independent of the sequence of the target nucleic acid. In some embodiments the second probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid. In some embodiments the third probe further comprises a target binding portion and a detectable portion and which provides a signal informative as to the probes location within the target, and further the detectable portion does not hybridize to the target nucleic acid, and the detectable portions composition may be independent of the sequence of the target nucleic acid. In certain embodiments the fourth probe further comprises a target binding portion and a detectable portion and which provides a signal informative as to its location within the target, and further where the detectable portion does not hybridize to the target nucleic acid, and the detectable portions composition may be independent of the sequence of the target nucleic acid.

Also provided, in part, is a method for haplotyping which uses one reaction and four separate probes for determining the haplotype of a target nucleic acid molecule comprising the steps of: (a) hybridizing at least a first probe to the 5' portion of a target nucleic acid; (b) hybridizing a second probe to the target nucleic acid 3' of the first probe where the first and second probes may be adjacent to a first sequence variation of the target nucleic acid sequence, and define a region there between, the region between the probes may comprise either no nucleotides, one nucleotide or more than one nucleotide; (c) providing in a reaction vessel a ligase and a labeled nucleotide or nucleotides which may be complementary to the target nucleic acid and ligating together the first probe, second probe and nucleotide(s) if the nucleotide(s) is complementary to the target nucleic acid; (d) hybridizing at least a third probe to a second 5' portion of the target nucleic acid; (e) hybridizing a fourth probe to the target nucleic acid 3' of the third probe where the third and fourth probes may be adjacent to a second sequence variation of the target nucleic acid sequence, and define a region there between, the region between the probes may comprise either no nucleotides, one nucleotide or more than one nucleotide, and further where the 3' portion of the third probe and the 5' portion of the fourth probe may be ligated to each other; (f) hybridizing a fourth probe to the target nucleic acid 3' of the third probe where the third and fourth probes may be adjacent to a second sequence variation of the target nucleic acid sequence, and define a region there between, the region between the probes may comprise either no nucleotides, one nucleotide or more than one nucleotide, and further where the 3' portion of the third probe and the 5' portion of the fourth probe may be ligated to each other; (g) providing in the reaction vessel a ligase and a labeled nucleotide or nucleotides which may be complementary to the target nucleic acid and ligating together the third probe, fourth probe and labeled nucleotide(s) if the nucleotide(s) is complementary to the target nucleic acid, whereby a complex comprising the ligated first probe, labeled nucleotides, second probe, the third probe, labeled nucleotides and fourth probe, and target nucleic acid is formed; (h) separating the complex of step (g) from the target nucleic acid to form a signal-generating complex; and (i) performing an analysis of the signal-generating complex of step (h) to provide a signal generating moiety pattern and where correlation of the signal generating moiety pattern with the location of the first, second, third and fourth probe, and analysis of the signal of the labeled nucleotides determines the haplotype of the target nucleic acid. The analysis in step (i) of signal-generating complexes may be performed by passage of the signal-generating complex through a nanopore, in certain embodiments.

Also provided, in part, is a method for sequencing which uses two reactions and two separate probes for determining the sequence of a target nucleic acid molecule comprising the steps of: (a) hybridizing at least a first probe to the 5' portion of a target nucleic acid; (b) hybridizing a second probe to the target nucleic acid 3' of the first probe where the first and second probes may be adjacent to at least one base of the target nucleic acid sequence, and define a region there between, and the region between the probes may comprise either no bases, one base or more than one base; (c) providing in a first reaction vessel a ligase or a ligase, a polymerase and a first nucleotide or nucleotides, the nucleotide or nucleotides which may be complementary to the target nucleic acid sequence and ligating together the first probe and second probe if the probes are complementary to the target nucleic acid or polymerizing the nucleotides and ligating together the first probe and second probe and nucleotide(s) if the nucleotide(s) is complementary to the target nucleic acid sequence; (d) providing in at least a second reaction vessel a ligase or a ligase, a polymerase, and a second nucleotide or nucleotides, the nucleotide or nucleotides which may be complementary to the target nucleic acid sequence and ligating together the first probe and second probe if the probes are complementary to the target nucleic acid or polymerizing the nucleotides and ligating together the first probe and second probe and nucleotide(s) if the nucleotide(s) is complementary to the target nucleic acid sequence, whereby a complex comprising either the ligated first probe and second probe and target nucleic acid or the ligated first probe, polymerized nucleotides, second probe and target nucleic acid is formed; (e) separating the complex formed as the result of step (c), step (d), or a combination thereof, from the target nucleic acid to form a signal-generating complex; and (f) performing an analysis of the signal-generating complex of step (e) to provide a signal generating moiety pattern and where correlation of the signal generating moiety pattern with the specific sequence of the first and second probe and the location of the first and the second probe, and determination of whether the signal-generating complex of step (e) has been formed in the first or the second reaction vessel or the first and the second reaction vessel determines the sequence of the target nucleic acid.

In certain embodiments using two reactions and two separate probes for determining the sequence of a target nucleic acid molecule, analysis in step (f) may be performed by passing a signal-generating complex through a nanopore. In some embodiments each of steps (a)-(e) may be performed in at least two or more reaction vessels for at least two separate first probes and two separate second probes, where each set of first probe and second probe can be specific for a target nucleic acid sequence, and provides a signal uniquely indicative of a specific target nucleic acid sequence and its location. In some embodiments, at least two separate first probes and two separate second probes can be designed to hybridize with an entire genome, whereby the sequence of an entire genome can be determined.

In some embodiments a first probe further comprises a target binding portion and a detectable portion which provides a signal informative as to the base sequence of the first probe, and the probes location within the target, and further where the detectable portion does not hybridize to the target nucleic acid, and the detectable portions composition may be independent of the sequence of the target nucleic acid. In certain embodiments a second probe further comprises a target binding portion and a detectable portion and which provides a signal informative as to the base sequence of the second probe, and the probes location within the target, and further where the detectable portion does not hybridize to the target nucleic acid, and the detectable portions composition may be independent of the sequence of the target nucleic acid.

Also provided, in part, is a method for sequencing which uses one reaction and two separate probes for determining the sequence of a target nucleic acid molecule comprising the steps of: (a) hybridizing at least a first probe to the 5' portion of a target nucleic acid; (b) hybridizing a second probe to the target nucleic acid 3' of the first probe where the first and second probes may be adjacent to at least one base of the target nucleic acid sequence, and define a region there between, and the region between the probes may comprise either no bases, one base or more than one base; (c) providing in a reaction vessel a ligase or a ligase, a polymerase, and a labeled nucleotide or nucleotides, the nucleotide or nucleotides which may be complementary to the target nucleic acid sequence and ligating together the first probe and second probe if the probes are complementary to the target nucleic acid or polymerizing the nucleotides and ligating together the first probe and second probe and nucleotide(s) if the nucleotide(s) is complementary to the target nucleic acid sequence, whereby a complex comprising either the ligated first probe, second probe and target nucleic acid or the ligated first probe, polymerized nucleotides, second probe and target nucleic acid is formed; (d) separating the complex of step (c) from the target nucleic acid to form a signal-generating complex; and (e) performing an analysis of the complex of step (c) or (d) to provide a signal generating moiety pattern and where correlation of the signal generating moiety pattern with the specific sequence of the first probe and the location of the first probe, and analysis of the signal of the nucleotide determines the sequence of the target nucleic acid.

In some embodiments using one reaction and two separate probes for determining the sequence of a target nucleic acid molecule the analysis in step (e) of a signal-generating complex is performed by passage of the signal-generating complex through a nanopore. In certain embodiments each of steps (a)-(d) may be performed in a single reaction vessel for at least two separate first probes and two separate second probes, where each set of first probe and second probe can be specific for a target nucleic acid sequence, and provides a signal uniquely indicative of the target nucleic acid sequence and its location. At least two separate first probes and two separate second probes can be designed to hybridize with an entire genome, whereby the sequence of an entire genome can be determined, in some embodiments.

Also provided, in part, is a method for sequencing which uses two reactions and one probe for determining the sequence of a target nucleic acid molecule comprising the steps of: (a) hybridizing at least a first probe to a portion of a target nucleic acid, where the probe may be adjacent to a base of the target nucleic acid; (b) providing in a first reaction vessel a polymerase and a first nucleotide or nucleotides which may be complementary to a base of the target nucleic acid and extending the probe with the nucleotide(s) if the nucleotide(s) is complementary to the base of the target nucleic acid; (c) providing in at least a second reaction vessel a ligase and a second nucleotide or nucleotides which may be complementary to the nucleotide of the target nucleic acid and extending the probe, and nucleotide(s) if the nucleotide(s) is complementary to the base of the target nucleic acid, whereby a complex comprising the extended probe, nucleotide(s) and target nucleic acid is formed; (d) separating the complex formed as the result of step (b), step (c), or a combination thereof, from the target nucleic acid to form a signal-generating complex; and (e) performing an analysis of the signal-generating complex of step (d) to provide a signal generating moiety pattern and where correlation of the signal generating moiety pattern with the specific sequence of the first probe and the location of the first probe, and determination of whether the signal-generating complex of step (d) has been formed in the first or the second reaction vessel or the first and the second reaction vessel determines the sequence of the target nucleic acid.

In some embodiments using two reactions and one probe for determining the sequence of a target nucleic acid molecule the analysis in step (e) of a signal-generating complex may be performed by passage of the signal-generating complex through a nanopore. In some embodiments the probe further comprises a target binding portion and a detectable portion and which provides a signal informative as to the base sequence of the probe, and the probes location within the target, and further where the detectable portion does not hybridize to the target nucleic acid, and the detectable portions composition may be independent of the sequence of the target nucleic acid.

Also provided, in part, is a method for sequencing which uses one reaction and one probe for determining the sequence of a target nucleic acid molecule comprising the steps of: (a) hybridizing at least a first probe to a portion of a target nucleic acid, where the probe may be adjacent to a base of the target nucleic acid; (b) providing in a reaction vessel a polymerase and a labeled nucleotide or nucleotides which may be complementary to the base of the target nucleic acid and extending the probe with the nucleotide(s) if the nucleotide(s) is complementary to the base of the target nucleic acid, whereby a complex comprising the extended probe, nucleotide(s) and target nucleic acid; (c) separating the complex of step (b) from the target nucleic acid to form a signal-generating complex; and (d) performing an analysis of the signal-generating complex of step (c) to provide a signal generating moiety pattern and where correlation of the signal generating moiety pattern with the specific sequence of the first probe and with the location of the first probe, and analysis of the signal of the nucleotide determines the sequence of the target nucleic acid. The analysis in step (d) of a signal-generating complex may be performed by passage of the signal-generating complex through a nanopore, in certain embodiments.

Also provided, in part, is a method for sequencing which uses two reactions and four probes for determining the sequence, generally of a larger region, of a target nucleic acid molecule comprising the steps of: (a) hybridizing at least a first probe to the 5' portion of a target nucleic acid; (b) hybridizing a second probe to the target nucleic acid 3' of the first probe where the first and second probes are adjacent to a first base of the target nucleic acid sequence, and define a region there between, the region between the probes may comprise either no bases, one base or more than one base; (c) providing in a first reaction vessel a ligase or a ligase, a polymerase and a first nucleotide or nucleotides, the nucleotide or nucleotides which may be complementary to the target nucleic acid and ligating together the first probe and second probe if the probes are complementary to the target nucleic acid or polymerizing the nucleotides and ligating together the first probe, second probe and polymerized nucleotide(s) if the nucleotide(s) is complementary to the target nucleic acid sequence; (d) providing in at least a second reaction vessel a ligase or a ligase, a polymerase, and a second nucleotide or nucleotides, the nucleotide or nucleotides which may be complementary to the target nucleic acid sequence and ligating together the first probe and second probe if the probes are complementary to the target nucleic acid or polymerizing the nucleotides and ligating together the first probe and second probe and polymerized nucleotide(s) if the nucleotide(s) is complementary to the target nucleic acid sequence; (e) hybridizing at least a third probe to a second 5' portion of the target nucleic acid; (f) hybridizing a fourth probe to the target nucleic acid 3' of the third probe where the third and fourth probes are adjacent to a second base of the target nucleic acid sequence, and define a region there between, the region between the probes may comprise either no bases, one base or more than one base, and further where the 3' portion of the third probe and the 5' portion of the fourth probe may be ligated to each other; (g) providing in the first reaction vessel a ligase or a ligase, a polymerase, and a nucleotide or nucleotides, the nucleotide or nucleotides which may be complementary to the target nucleic acid sequence and ligating together the third probe and fourth probe if the probes are complementary to the target nucleic acid or polymerizing the nucleotides and ligating together the third probe and fourth probe and polymerized nucleotide(s) if the nucleotide(s) is complementary to the target nucleic acid sequence; (h) providing in the at least second reaction vessel a ligase or a ligase, a polymerase, and a nucleotide or nucleotides, the nucleotide or nucleotides which may be complementary to the target nucleic acid sequence and ligating together the third probe and fourth probe if the probes are complementary to the target nucleic acid or polymerizing the nucleotides and ligating together the third probe, fourth probe and polymerized nucleotide(s) if the nucleotide(s) is complementary to the target nucleic acid sequence, whereby a complex comprising either one of: 1) the ligated first probe and second probe of step (c), and the target nucleic acid or 2) the ligated first probe, polymerized nucleotides, second probe of step (c), and the target nucleic acid; and either one of 3) the ligated third probe and fourth probe of step (g), and the target nucleic acid or 4) the ligated third probe, polymerized nucleotides, fourth probe of step (g) and the target nucleic acid is formed or a complex comprising either one of: 1) the ligated first probe and second probe of step (d), and the target nucleic acid or 2) the ligated first probe, polymerized nucleotides, second probe of step (d), and target nucleic acid; and either one of 3) the ligated third probe and fourth probe of step (h), and the target nucleic acid or 4) the ligated third probe, polymerized nucleotides, fourth probe of step (h) and target nucleic acid is formed; (i) separating any of the complexes, from the target nucleic acid to form a signal-generating complex; and (j) performing an analysis of the signal-generating complex to provide a signal generating moiety pattern and where correlation of the signal generating moiety pattern with the specific base sequence of the first, second, third and fourth probe, and determination of whether the signal-generating complex has been formed in the first or the second reaction vessel or the first and the second reaction vessel determines the sequence of the target nucleic acid.

In certain embodiments using two reactions and four probes for determining the sequence, generally of a larger region, of a target nucleic acid molecule, the analysis in step (j) of any of the signal-generating complexes of step (g), step (h), or combinations thereof, may be performed by passage of any of the signal-generating complexes through a nanopore. In some embodiments the first probe further comprises a target binding portion and a detectable portion that provide a signal informative as to the base sequence of the probe, and the probes location within the target, and further where the detectable portions do not hybridize to the target nucleic acid, and the detectable portions composition may be independent of the sequence of the target nucleic acid. In some embodiments the second probe further comprises a target binding portion and a detectable portion that provide a signal informative as to the base sequence of the probe, and the probes location within the target, and further where the detectable portions do not hybridize to the target nucleic acid, and the detectable portions composition may be independent of the sequence of the target nucleic acid. In some embodiments the third probe further comprises a target binding portion and a detectable portion that provide a signal informative as to the base sequence of the probe, and the probes location within the target, and further where the detectable portions do not hybridize to the target nucleic acid, and the detectable portions composition may be independent of the sequence of the target nucleic acid. In some embodiments the fourth probe further comprises a target binding portion and a detectable portion that provide a signal informative as to the base sequence of the probe, and the probes location within the target, and further where the detectable portions do not hybridize to the target nucleic acid, and the detectable portions composition may be independent of the sequence of the target nucleic acid.

Also provided, in part, is a method for sequencing which uses one reaction and four probes for determining the sequence, generally of a larger region, of a target nucleic acid molecule comprising the steps of: (a) hybridizing at least a first probe to the 5' portion of a target nucleic acid; (b) hybridizing a second probe to the target nucleic acid 3' of the first probe where the first and second probes are adjacent to a first base of the target nucleic acid sequence, and define a region there between, the region between the probes may comprise either no bases, one base or more than one base; (c) providing in a reaction vessel a ligase and a labeled nucleotide or nucleotides which may be complementary to a nucleotide of the target nucleic acid and ligating together the first probe, second probe and nucleotide(s) if the nucleotide(s) is complementary to the target nucleic acid; (d) hybridizing at least a third probe to a second 5' portion of the target nucleic acid; (e) hybridizing a fourth probe to the target nucleic acid 3' of the third probe where the third and fourth probes are adjacent to a second base of the target nucleic acid sequence, and define a region there between, the region between the probes may comprise either no bases, one base or more than one base, and further where the 3' portion of the third probe and the 5' portion of the fourth probe may be ligated to each other; (f) providing in the reaction vessel a ligase and a labeled nucleotide or nucleotides which may be complementary to nucleotides of the target nucleic acid and ligating together the third probe, fourth probe and labeled nucleotide(s) if the nucleotide(s) is complementary to the target nucleic acid, whereby a complex comprising the ligated first probe, labeled nucleotides, second probe, the third probe, labeled nucleotides, fourth probe and target nucleic acid is formed; (g) separating the complex of step (f) from the target nucleic acid to form a signal-generating complex; and (h) performing an analysis of the signal-generating complex provide a signal generating moiety pattern and where correlation of the signal generating moiety pattern with the specific base sequence of the first, second, third and fourth probe, and analysis of the signal of the labeled nucleotides determines the sequence of the target nucleic acid. The analysis in step (h) of any of the signal-generating complexes of step (f) may be performed by passage of any of the signal-generating complexes through a nanopore, in certain embodiments.

Also provided, in part, is a method for determining whether a methylation-based sequence variation of a target nucleic acid molecule has been generated, comprising the steps of: (a) treating target nucleic acids with an agent to convert non-methylated cytosine to uracil; (b) hybridizing at least a first probe to the 5' portion of a target nucleic acid; (c) hybridizing a second probe to the target nucleic acid 3' of the first probe where the first and second probes are adjacent to the methylation-based sequence variation and define a region there between, where the region between the probes may comprise either no nucleotides, one nucleotide or more than one nucleotide; (d) providing in a first reaction vessel a ligase or a ligase, a polymerase and a first nucleotide or nucleotides, the first nucleotide or nucleotides which may be complementary to the methylation-based sequence variation and ligating together the first probe and second probe if the probes are complementary to the target nucleic acid or polymerizing the nucleotide(s) and ligating together the first probe and second probe and nucleotides(s) if the nucleotide(s) is complementary to the methylation-based sequence variation; (e) providing in at least a second reaction vessel a ligase or a ligase, a polymerase and a second nucleotide or nucleotides, the nucleotide or nucleotides which may be complementary to the methylation-based sequence variation and ligating together the first probe and second probe if the probes and nucleotide(s) are complementary to the target nucleic acid or polymerizing the nucleotides and ligating together the first probe and second probe and nucleotide(s) if the nucleotide(s) is complementary to the methylation-based sequence variation, whereby a complex comprising either the ligated first probe and second probe, and target nucleic acid or the ligated first probe and polymerized nucleotides and second probe, and target nucleic acid, is formed; (f) separating the complex of step (e) from the target nucleic acid to form a signal-generating complex; and (g) performing an analysis of the signal-generating complex of step (f) to provide a signal generating moiety pattern and where correlation of the signal generating moiety pattern with the location of the first and the second probe, and determination of whether the signal-generating complex of step (f) has been formed in the first or the second reaction vessel or the first and the second reaction vessel determines the methylation-based sequence variation.

In certain embodiments for determining whether a methylation-based sequence variation of a target nucleic acid molecule has been generated, analysis in step (g) may be performed by passing a signal-generating complex through a nanopore. In certain embodiments a first probe is complementary to a target nucleic acid at a sequence variation. In certain embodiments at least two first probes are introduced to the reaction vessel of step (b), and in step (a) only the first probe that is complementary to the sequence variation hybridizes to the target nucleic acid. In certain embodiments, multiplexing of the methods disclosed herein may be performed; for example, each of steps (a)-(f) may be performed in at least two or more reaction vessels for at least two separate first probes and two separate second probes, where each set of first probe and second probe can be specific for a separate methylation-based sequence variation, and provides a signal uniquely indicative of a specific sequence variation and its location. A set of first probes and second probes may constitute a set of probes sufficient to provide information about methylation-based sequence variations of an entire genome, in some embodiments.

In some embodiments the first probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid. In some embodiments the second probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid.

Also provided, in part, is a method for methylation analysis which uses two reactions and one probe for determining a methylation-based sequence variation of a target nucleic acid molecule comprising the steps of: (a) treating target nucleic acids with an agent to convert non-methylated cytosine to uracil; (b) hybridizing at least a first probe to the 5' portion of a target nucleic acid, where the probe may be adjacent to a methylation-based sequence variation; (c) providing in a reaction vessel a polymerase and a labeled nucleotide or nucleotides which may be complementary to a methylation-based sequence variation and extending the probe with the nucleotide(s) if the nucleotide(s) is complementary to the methylation-based sequence variation; (d) providing in at least a second reaction vessel a polymerase and a second nucleotide or nucleotides which may be complementary to the methylation-based sequence variation and extending the probe with nucleotide(s) if the nucleotide(s) is complementary to the methylation-based sequence variation, whereby a complex comprising the extended probe and nucleotide(s), and target nucleic acid is formed; (e) separating the complex of step (d) from the target nucleic acid to form a signal-generating complex; and (f) performing an analysis of the signal-generating complex of step (e) to provide a signal generating moiety pattern and where correlation of the signal generating moiety pattern with the location of the first probe, and determination of whether the complex of step (e) has been formed in the first or the second reaction vessel or the first and the second reaction vessel determines the methylation-based sequence variation.

In some embodiments using two reactions and one probe for determining a methylation-based sequence variation of a target nucleic acid molecule, the analysis in step (f), of a signal-generating complex, may be performed by passage of the signal-generating complex through a nanopore, in some embodiments. In some embodiments the probe further comprises a target binding portion and a detectable portion and which provides a signal informative as to the probes location within the target nucleic acid, and further where the detectable portion does not hybridize to the target nucleic acid, and the probes composition may be independent of the sequence of the target nucleic acid.

Also provided, in part, is a method for methylation analysis which uses one reaction and two probes for determining a methylation-based sequence variation of a target nucleic acid molecule comprising the steps of: (a) treating target nucleic acids with an agent to convert non-methylated cytosine to uracil; (b) hybridizing at least a first probe to the 5' portion of a target nucleic acid, where the probe may be adjacent to a methylation-based sequence variation; (c) hybridizing a second probe to the target nucleic acid 3' of the first probe where the first and second probes may be adjacent to a methylation-based sequence variation, and define a region there between, and the region between the probes may comprise either no bases, one base or more than one base; (d) providing in a reaction vessel a ligase or a ligase, a polymerase and a labeled nucleotide or nucleotides, the nucleotide or nucleotides which may be complementary to the methylation-based sequence variation and ligating together the first probe and second probe if the probes are complementary to the target nucleic acid or polymerizing nucleotides and ligating together the first probe and second probe and nucleotide(s) if the nucleotide(s) is complementary to the methylation-based sequence variation, whereby a complex comprising either the ligated first probe and second probe and target nucleic acid or the ligated first probe and polymerized nucleotides and second probe and target nucleic acid is formed; (e) separating the complex of step (d) from the target nucleic acid to form a signal-generating complex; and (f) performing an analysis of the signal-generating complex of step (e) to provide a signal generating moiety pattern and where correlation of the signal generating moiety pattern with the location of the first and the second probe, and analysis of the signal of the nucleotide determines the methylation-based sequence variation.

In some embodiments using one reaction and two probes for determining a methylation-based sequence variation of a target nucleic acid molecule, the analysis in step (f) of a signal-generating complex may be performed by passage of the signal-generating complex through a nanopore. In some embodiments each of steps (a)-(e) may be performed simultaneously and in the same reaction vessel for at least two separate first probes and two separate second probes, where each set of first probe and second probe can be specific for a separate methylation-based sequence variation, and provides a signal uniquely indicative of a specific sequence variation and its location. In some embodiments a first probe may further comprise a target binding portion and a detectable portion and which provides a signal informative as to the probes location within the target and further where the detectable portion does not hybridize to the target nucleic acid, and the detectable portions composition may be independent of the sequence of the target nucleic acid. In certain embodiments a second probe may further comprise a target binding portion and a detectable portion and which provides a signal informative as to the probes location within the target, and further where the detectable portion does not hybridize to the target nucleic acid, and the detectable portions composition may be independent of the sequence of the target nucleic acid.

Also provided, in part, is a method for methylation analysis which uses one reaction and one probe for determining a methylation-based sequence variation of a target nucleic acid molecule comprising the steps of: (a) treating target nucleic acids with an agent to convert non-methylated cytosine to uracil; (b) hybridizing at least a first probe to the 5' portion of a target nucleic acid, where the probe may be adjacent to a methylation-based sequence variation; (c) providing in a reaction vessel a polymerase and a labeled nucleotide or nucleotides which may be complementary to a methylation-based sequence variation and extending the probe with the nucleotide(s) if the nucleotide(s) is complementary to the methylation-based sequence variation, whereby a complex comprising the extended probe and nucleotide(s), and target nucleic acid is formed; (d) separating the complex of step (c) from the target nucleic acid to form a signal-generating complex; and (e) performing an analysis of the signal-generating complex of step (d) to provide a signal generating moiety pattern and where correlation of the signal generating moiety pattern with the location of the first probe, and analysis of the signal of the nucleotide determines the sequence variation. In certain embodiments the analysis in step (e) of a signal-generating complex may be performed by passage of the signal-generating complex through a nanopore.

Also provided, in part, is a method for methylation analysis of pooled samples comprising the steps of: (a) obtaining a first pool of nucleic acid containing a target nucleic acid, where the nucleic acid in the first pool has a first methylation status, and obtaining a second pool of nucleic acid containing a target nucleic acid where the nucleic acid in the second pool has a second methylation status; (b) enriching the target nucleic acid of the first pool for those target nucleic acids which are methylated, and enriching the target nucleic acid of the second pool for those target nucleic acids which are methylated; (c) comparing the methylation status of the first pool and the second pool by treating the target nucleic acid in each pool with an agent to convert non-methylated cytosine to uracil; (d) hybridizing at least a first probe to the 5' portion of the target nucleic acid in each pool; (e) hybridizing a second probe to the target nucleic acid 3' of the first probe for each pool where the first and second probes are adjacent to a methylation-based sequence variation and define a region there between, where the region between the probes may comprise either no nucleotides, one nucleotide or more than one nucleotide; (f) providing, for each pool, in a first reaction vessel a ligase or a ligase, a polymerase and a first nucleotide or nucleotides, the first nucleotide or nucleotides which may be complementary to the methylation-based sequence variation and ligating together the first probe and second probe if the probes are complementary to the target nucleic acid or polymerizing the nucleotide(s) and ligating together the first probe and second probe and nucleotides(s) if the nucleotide(s) is complementary to the methylation-based sequence variation; (g) providing, for each pool, in at least a second reaction vessel a ligase or a ligase, a polymerase and a second nucleotide or nucleotides, the nucleotide or nucleotides which may be complementary to the methylation-based sequence variation and ligating together the first probe and second probe if the probes and nucleotide(s) are complementary to the target nucleic acid or polymerizing the nucleotides and ligating together the first probe and second probe and nucleotide(s) if the nucleotide(s) is complementary to the methylation-based sequence variation, whereby, for each pool, a complex comprising either the ligated first probe and second probe, and target nucleic acid or the ligated first probe and polymerized nucleotides and second probe, and target nucleic acid, is formed; (h) separating the complex of step (g) from the target nucleic acid to form a signal-generating complex for each pool; and (i) performing an analysis of the signal-generating complex of step (h) for each pool to provide a signal generating moiety pattern and where correlation of the signal generating moiety pattern with the location of the first and the second probe, and determination of whether the signal-generating complex of step (h) has been formed in the first or the second reaction vessel or the first and the second reaction vessel determines the methylation-based sequence variation of each pool and thereby the methylation status of each pool.

In some embodiments the first pool and the second pool originate from the same individual. In certain embodiments the first pool and the second pool originate from different individuals (e.g., fetal nucleic acid from maternal serum, plasma or whole blood). In some embodiments the first pool and the second pool are obtained from the same sample, but represent different fractions obtained from a methylated-nucleic acid-binding-agent column. In certain embodiments quantitative methylation analysis is possible. A difference in degree of methylation between pools can be reflected in the amount of signal-generating moiety created so that by analyzing the number of particular signals obtained in each pool over some period of time you can determine the quantitative difference in methylation between the pools, for example. In some embodiments the first probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid. In certain embodiments the second probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid.

Also provided, in part, is a method for methylation analysis using a methylated-nucleic-acid-binding-agent, comprising the steps of: (a) hybridizing at least a first probe to the 5' portion of the target nucleic acid in the presence of a methylated-nucleic-acid-binding-agent, whereby if a methylation-based sequence variation is a non-methylated sequence variation the probe will bind, and if it is a methylated-sequence variation the probe will not bind; (b) hybridizing a second probe to the target nucleic acid 3' of the first probe where the first and second probes are adjacent to the methylation-based sequence variation and define a region there between, where the region between the probes may comprise either no nucleotides, one nucleotide or more than one nucleotide; (c) providing in a first reaction vessel a ligase or a ligase, a polymerase and a first nucleotide or nucleotides, the first nucleotide or nucleotides which may be complementary to the methylation-based sequence variation and ligating together the first probe and second probe if the probes are complementary to the target nucleic acid or polymerizing the nucleotide(s) and ligating together the first probe and second probe and nucleotides(s) if the nucleotide(s) is complementary to the methylation-based sequence variation; (d) providing in at least a second reaction vessel a ligase or a ligase, a polymerase and a second nucleotide or nucleotides, the nucleotide or nucleotides which may be complementary to the methylation-based sequence variation and ligating together the first probe and second probe if the probes and nucleotide(s) are complementary to the target nucleic acid or polymerizing the nucleotides and ligating together the first probe and second probe and nucleotide(s) if the nucleotide(s) is complementary to the methylation-based sequence variation, whereby a complex comprising either the ligated first probe and second probe, and target nucleic acid or the ligated first probe and polymerized nucleotides and second probe, and target nucleic acid, is formed; (e) separating the complex of step (d) from the target nucleic acid to form a signal-generating complex; and (f) performing an analysis of the signal-generating complex of step (e) to determine that there is either no signal if the methylation-based sequence variation is a methylated variation or obtaining a signal generating moiety pattern where correlation of the signal generating moiety pattern with the location of the first and the second probe, and determination of whether the signal-generating complex of step (e) has been formed in the first or the second reaction vessel or the first and the second reaction vessel determines the methylation-based sequence variation if the methylation-based sequence variation is a non-methylated variation.

In some embodiments the methylated-nucleic-acid-binding-agent is selected from the group consisting of a protein, an antibody, a chemical agent. In certain embodiments the binding agent preferentially binds non-methylated nucleic acids. In some embodiments a first probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid. In certain embodiments the second probe further comprises a target binding portion and a detectable portion and which provides a signal informative as to the probes location within the target, and further where the detectable portion does not hybridize to the target nucleic acid, and the detectable portions composition may be independent of the sequence of the target nucleic acid.

In some methylation analysis embodiments, a probe or primer can have 1, 2, 3, or more mismatches, provided that the probe or primer can be used to amplify at least one nucleic acid target gene molecule desired to be amplified. For example, a nucleic acid target gene molecule can have three cytosine nucleotides in the region with which a primer hybridizes; when only one of the three C nucleotides are methylated, treatment with bisulfite can convert the two unmethylated C nucleotides to U nucleotides, and a primer 100% complementary to a nucleic acid target gene molecule having three C nucleotides can still hybridize to a nucleic acid target gene molecule having only one C nucleotide, such that the nucleic acid target gene molecule having only one C nucleotide can still be amplified.

Embodiments described herein are also useful for quantitative gene expression analysis. Thus, provided, in part, is a method for determining and adjusting the expression of at least two different target nucleic acid molecules, comprising the steps of: (a) preparing a sample by adding a known amount of a first standard nucleic acid having a nucleotide sequence at least one base different than a first target nucleic acid sequence to a biological specimen containing the first target nucleic acid, thereby creating a site of differentiation between the target and the standard nucleic acid; (b) amplifying the sample of step (a); (c) enhancing the difference between the first standard and the first target nucleic acid sequence at the site of differentiation; (d) quantifying the enhanced products of step (c) by measuring the ratio of the amplified first target nucleic acid to the amplified first standard nucleic acid to measure the amount of target nucleic acid sequence present in the biological sample; (e) preparing a sample by adding a known amount of a second standard nucleic acid having a nucleotide sequence at least one base different than a second target nucleic acid sequence to a biological specimen containing the second target nucleic acid, thereby creating a site of differentiation between the target and the standard nucleic acid; (f) amplifying the sample of step (e); (g) enhancing the difference between the second standard and the second target nucleic acid sequence at the site of differentiation; (h) quantifying the enhanced products of step (g) by measuring the ratio of the amplified target nucleic acid to the amplified standard nucleic acid to measure the amount of target nucleic acid sequence present in the biological sample; (i) comparing the quantity of step (d) to the quantity of step (h), and if the quantity in step (h) is greater than the quantity in step (d), then repeating steps (a)-(c) with a concentration of the first standard and first target nucleic acids which is reduced by the ratio of the quantity of step (d) over step (h), or if the quantity in step (d) is greater than the quantity in step (h), then repeating steps (e)-(g) with a concentration of the second standard and second target nucleic acids which is reduced by the ratio of the quantity of step (h) over step (d).

Embodiments described herein may be used to prepare compositions comprising genotype or allele-specific probes or compositions useful for sequencing. Thus provided are non-limiting examples of compositions comprising genotype or allele-specific probes or compositions useful for sequencing including; (1) nucleic acid probes comprising a target binding portion and further comprising at least one detectable portion attached thereto, where the detectable portion provides a signal informative as to the location of the probe within the target, and (2) nucleic acid probes comprising a target binding portion and further comprising at least one detectable portion attached thereto, where the detectable portion provides a signal informative as to the base sequence of the probe and the location of the probe within the target, and further where the detectable portion does not hybridize to the target nucleic acid, and its composition may be independent of the sequence of the target nucleic acid. In certain embodiments, the compositions may contain regions suitable for ligating or otherwise covalently or non-covalently joining multiple nucleic acid probes to each other. In some embodiments the signal-generating moiety is sufficiently unique to allow the simultaneous detection of at least 1024 unique base sequences.

In some embodiments the detectable portion of a nucleic acid probe does not hybridize to the target nucleic acid, and the detectable portions composition may be independent of the sequence of the target nucleic acid, and additionally where the composition comprises at least a portion of single-stranded nucleic acid suitable for initiation of threading of the composition through a nanopore. In any of the previous embodiments the one or more signal generating complexes may be separated from unhybridized oligonucleotides.

In some embodiments, compositions may contain regions suitable for ligating or otherwise covalently or non-covalently joining multiple nucleic acid probes to each other. Non-limiting examples of compositions containing regions suitable for ligating or otherwise covalently or non-covalently joining multiple nucleic acid probes to each other include compositions comprising: (a) a first nucleic acid probe having a 3' end and a 5' end and comprising a target binding portion and further comprising at least one detectable portion attached thereto, where the detectable portion provides a signal informative as to the base sequence of the probe and the location of the probe within the target, and further where the detectable portion does not hybridize to the target nucleic acid, and the detectable portions composition may be independent of the sequence of the target nucleic acid; (b) a second nucleic acid probe having a 3' end and a 5' end and comprising a target binding portion and further comprising at least one detectable portion attached thereto, where the detectable portion provides a signal informative as to the base sequence of the probe and the location of the probe within the target, and further where the detectable portion does not hybridize to the target nucleic acid, and the detectable portions composition may be independent of the sequence of the target nucleic acid, where the first and second probe are ligated to each other; (c) a third nucleic acid probe having a 3' end and a 5' end and comprising a target binding region and further comprising at least one detectable portion attached thereto, where the detectable portion provides a signal informative as to the base sequence of the probe and the location of the probe within the target, and further where the detectable portion does not hybridize to the target nucleic acid, and the detectable portions composition may be independent of the sequence of the target nucleic acid; (d) a fourth nucleic acid probe having a 3' end and a 5' end and comprising a target binding portion and further comprising at least one detectable portion attached thereto, where the detectable portion provides a signal informative as to the base sequence of the probe and the location of the probe within the target, and further where the detectable portion does not hybridize to the target nucleic acid, and the detectable portions composition may be independent of the sequence of the target nucleic acid, where the third and fourth probe are ligated to each other; (e) further where the 3' end of the second probe and the 5' end of the third probe are ligated together. In any of the previous embodiments a composition may comprise at least a portion of single-stranded nucleic acid suitable for initiation of threading of the composition through a nanopore.

Also provided, in part, is a method for analyzing a genetic sequence variation or a sequence of a target nucleic acid comprising the steps of: (a) in a first solution phase, hybridizing to a target nucleic acid at least one probe comprising a target binding portion and further comprising at least one detectable portion attached thereto; and (b) analyzing the genetic variation or sequence using the first or a second solution-phase-based analysis method. In some embodiments the detectable portion of the probe provides a signal informative as to the location of the probe within the target, and further where the detectable portion does not hybridize to the target nucleic acid and the detectable portions composition may be independent of the sequence of the target nucleic acid. In certain embodiments the solution-phase-based analysis method is nanopore sequencing. In some embodiments the timing between signal generating moieties may be analyzed. In some embodiments, any of the previously described probes may be used for analyzing a genetic sequence variation or a sequence of a target nucleic acid. In some embodiments the sequencing method may be pyrosequencing. In certain embodiments the sequencing method may be based on sequencing by synthesis.

The term "polymorphism" as used herein refers to an allelic variant. Polymorphisms can include single nucleotide polymorphisms (SNPs) as well as simple sequence length polymorphisms. A polymorphism can be due to one or more nucleotide substitutions at one allele in comparison to another allele or can be due to an insertion or deletion.

The term "cleavage agent" as used herein refers to any means that is capable of cleaving a detector oligonucleotide to yield degradation products, including, but not limited to enzymes. For methods where amplification does not occur, the cleavage agent may serve solely to cleave, degrade or otherwise release the detector oligonucleotide or fragments thereof. The cleavage agent may be an enzyme. The cleavage agent may be natural, synthetic, unmodified or modified. For methods where amplification occurs, the cleavage agent is preferably an enzyme that possesses synthetic (or polymerization) activity and nuclease activity. Such an enzyme is often a nucleic acid amplification enzyme. An example of a nucleic acid amplification enzyme is a nucleic acid polymerase enzyme such as *Thermus aquaticus* (Taq) DNA polymerase (TaqMAN®) or *E. coli* DNA polymerase I. The enzyme may be naturally occurring, unmodified or modified. The term "polymerase" refers to an enzyme that catalyzes polynucleotide synthesis by addition of nucleotide units to a nucleotide chain using DNA or RNA as a template. The term refers to either a complete enzyme or a catalytic domain As used herein, a "subject" includes, but is not limited to, an animal, plant, bacterium, virus, parasite and any other organism or entity that has nucleic acid. Among animal subjects are mammals, including primates, such as humans. As used herein, "subject" may be used interchangeably with "patient" or "individual".

As used herein, "normal", when referring to a nucleic acid molecule or sample source, such as an individual or group of individuals, refers to a nucleic acid molecule or sample source that was not selected according to any particular criterion, and generally refers to a typical nucleotide sequence of a nucleic acid molecule or health condition of a sample source (e.g., one or more healthy subjects or one or more subjects that do not a disease). For example, a normal methylation state of a particular nucleotide locus can be the wild type methylation state of the nucleotide locus. In another example, a group of normal subjects can be a group of subjects not having a particular phenotype (such as a disease).

As used herein, a "phenotype" refers to a set of parameters that includes any distinguishable trait of an organism. A phenotype can be physical traits and/or mental traits, such as emotional traits. A phenotype may also include a subject's disease diagnosis, prognosis or therapeutic response.

The following documents hereby are incorporated by reference: WO 2006/020775; U.S. Pat. No. 5,795,782; U.S. Pat. No. 6,015,714; U.S. Pat. No. 6,362,002; U.S. Pat. No. 6,673,615; U.S. Pat. No. 6,627,067; U.S. Pat. No. 7,189,503; 20060063171A1; U.S. Pat. No. 6,464,842; WO04/078640; U.S. Pat. No. 6,267,872; U.S. Pat. No. 6,746,594; U.S. Pat. No. 6,723,513; WO 06/092588 U.S. Pat. No. 5,925,517; U.S. Pat. No. 6,150,097; U.S. Pat. No. 6,528,258; WO2005/045392; U.S. Pat. No. 6,706,204; U.S. Pat. No. 7,279,337; U.S. Pat. No. 7,030,167; U.S. Pat. No. 7,075,161; U.S. Pat. No. 6,210,896; U.S. Pat. No. 6,263,286; U.S. Pat. No. 6,355,420; U.S. Pat. No. 6,403,311; U.S. Pat. No. 6,772,070; U.S. Pat. No. 6,927,065; U.S. Pat. No. 6,952,651; U.S. Pat. No. 7,005,264; 20050019784; 20060019247; U.S. Pat. No. 4,962,037; U.S. Pat. No. 6,537,755; U.S. Pat. No. 6,864,052.

The entirety of each patent, patent application, publication, document, GENBANK sequence, and other published material referenced herein hereby is incorporated by reference, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents. All patents and publications mentioned herein are indicative of the skill levels of those of ordinary skill in the art to which the invention pertains.

Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions that have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claim(s) that follow(s).

What is claimed is:

1. A method for analyzing a nucleic acid, which comprises:
   (a) contacting a target nucleic acid with a plurality of nucleic acid probes under conditions in which probes having a nucleotide sequence substantially complementary to a subsequence of the target nucleic acid (complementary nucleotide sequence) can hybridize to the target nucleic acid, wherein:
      (i) the complementary nucleotide sequence is located at the 5' or 3' end of each probe;
      (ii) the plurality of nucleic acid probes comprises probe pairs, wherein the ends of each complementary nucleotide sequence of each probe in a probe pair are (1) adjacent to one another when hybridized to the target nucleic acid, (2) are adjacent to an intervening linker probe and (3) do not abut one another and intervening nucleotides are added by an enzyme capable of polymerizing nucleotides complementary to the target nucleic acid sequence;
      (iii) each probe comprises a detector region having a polynucleotide sequence not substantially complementary to a subsequence of the target nucleic acid;
      (iv) each detector region is located at the 5' or 3' end of each probe and on the end of the probe opposite the complementary nucleotide sequence;
      (v) the end of a detector region of a first probe of a probe pair is in proximity to the end of a detector region of a second probe of a different probe pair, with the proviso that the end of a detector region of at least one of the other probes of the two probe pairs is not in proximity to the end of the detector region of any other probe; and
      (vi) the first probe flanks the second probe when the first probe and second probe are hybridized to the target nucleic acid;
   (b) ligating the ends of the complementary nucleotide sequences of probe pairs that are adjacent to one another when hybridized to the target nucleic acid;
   (c) joining the ends of detector regions in proximity to one another, thereby forming a linked probe molecule;
   (d) passing the linked probe molecule through the pore of a nanopore device; and
   (e) determining the base sequence of the linked probe molecule, whereby the target nucleic acid is analyzed.

2. The method of claim 1, wherein the target nucleic acid analysis is selected from the group consisting of: nucleic acid sequencing, copy number determination, methylation analysis, genotyping, haplotyping, identification of insertions, deletions, or translocations, identification of single nucleotide polymorphisms and sequence variations, detection of allelic variance, measurement of phenotypic variance, and combinations thereof.

3. The method of claim 1, wherein the target nucleic acid comprises DNA.

4. The method of claim 3, wherein the target nucleic acid consists of DNA.

5. The method of claim 1, wherein the target nucleic acid is from a single sample.

6. The method of claim 1, wherein the target nucleic acid comprises pooled DNA.

7. The method of claim 6, wherein the target nucleic acid consists of pooled DNA.

8. The method of claim 1, wherein the target nucleic acid is fragmented DNA.

9. The method of claim 1, wherein the target nucleic acid is methylated DNA.

10. The method of claim 9, wherein the target nucleic acid is treated with an agent that converts one or more non-methylated nucleotides, or methylated nucleotides, in the target nucleic acid to a detectable entity.

11. The method according to claim 10, wherein the target nucleic acid is treated with an agent that converts non-methylated cytosine to uracil.

12. The method of claim 1, wherein the target nucleic acid comprises RNA.

13. The method of claim 12, wherein the target nucleic acid consists of RNA.

14. The method of claim 1, wherein the target nucleic acid comprises pooled RNA.

15. The method of claim 14, wherein the target nucleic acid consists of pooled RNA.

16. The method of claim 1, wherein one or more probes comprise(s) DNA.

17. The method of claim 16, wherein one or more probes consist(s) of DNA.

18. The method of claim 1, wherein one or more probes comprise(s) RNA.

19. The method of claim 18, wherein one or more probes consist(s) of RNA.

20. The method of claim 1, wherein one or more probes comprise(s) PNA.

21. The method of claim 20, wherein one or more probes consist(s) of PNA.

22. The method of claim 1, wherein the detector region of one or more probes comprise(s) a detectable moiety.

23. The method of claim 22, wherein the detectable moiety is selected from the group consisting of: a radioactive agent, a fluorescent agent, a light scattering agent, a molecular beacon, an affinity capture agent, a chemiluminescent agent, a protein, a peptide, a chromogenic agent, a biomolecule, and a combination thereof.

24. The method of claim 1, wherein the portions of the detector regions of probes in proximity to one another are joined by chemical ligation.

25. The method of claim 1, wherein the portions of the detector regions of probes in proximity to one another are joined by cross-linking.

26. The method of claim 1, wherein the linked probe molecule is passed through the nanopore device by a gradient.

27. The method of claim 26, wherein the gradient is an electrical gradient, chemical gradient, magnetic gradient, or a combination thereof.

28. The method of claim 1, wherein the base sequence of the linked probe molecule is determined by a signal from a detector region or by a nucleotide sequencing method.

29. The method of claim 28, wherein the base sequence is determined by a nucleotide sequencing method and the nucleotide sequencing method is pyrosequencing.

30. The method of claim 28, wherein the base sequence is determined by a nucleotide sequencing method and the nucleotide sequencing method is sequencing by synthesis.

31. The method of claim 25, wherein the cross-linking is effected by UV light.

32. The method of claim 25, wherein the cross-linking is effected by a non-specific cross-linking agent.

33. The method of claim 25, wherein the cross-linking is effected by a sequence-specific cross-linking agent.

34. The method of claim 25, wherein the cross-linking is effected by ligation.

35. The method of claim 25, wherein the cross-linking is effected by a chemical cross-linking agent.

* * * * *